United States Patent
Lu et al.

(10) Patent No.: US 9,649,358 B2
(45) Date of Patent: May 16, 2017

(54) METHODS FOR USE OF NEURAL STEM CELL COMPOSITIONS FOR TREATMENT OF CENTRAL NERVOUS SYSTEM LESIONS

(71) Applicant: THE REGENTS OF THE UNIVERSITY OF CALIFORNIA, Oakland, CA (US)

(72) Inventors: Paul Lu, San Diego, CA (US); Mark H. Tuszynski, La Jolla, CA (US)

(73) Assignees: The Regents of the University of California, Oakland, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/362,891

(22) PCT Filed: Dec. 10, 2012

(86) PCT No.: PCT/US2012/068807
§ 371 (c)(1),
(2) Date: Jun. 4, 2014

(87) PCT Pub. No.: WO2013/090205
PCT Pub. Date: Jun. 20, 2013

(65) Prior Publication Data
US 2014/0308256 A1 Oct. 16, 2014

Related U.S. Application Data

(60) Provisional application No. 61/569,564, filed on Dec. 12, 2011.

(51) Int. Cl.
*A61K 38/18* (2006.01)
*A61K 35/30* (2015.01)

(52) U.S. Cl.
CPC ............ *A61K 38/185* (2013.01); *A61K 35/30* (2013.01); *A61K 38/18* (2013.01)

(58) Field of Classification Search
None
See application file for complete search history.

(56) References Cited

U.S. PATENT DOCUMENTS

2010/0021437 A1  1/2010  Isacson et al.

FOREIGN PATENT DOCUMENTS

WO  WO 2003/000852 A2  1/2003

OTHER PUBLICATIONS

Kuh et al., Acta Neurochir, 147:985-992, Jul. 11, 2005.*
Iwanami et al., Journal of Neuroscience Research, 80:182-190, 2005.*
Salewski et al., J Cell Physiol, 222: 515-521, 2010.*
Mothe et al., PLoS ONE 9(11):e27079, Nov. 2, 2011.*
Schwab, Science, vol. 295, Feb. 8, 2002.*
Lu et al., Neural stem cells constitutively secrete neurotrophic factors and promote extensive host axonal growth after spinal cord injury, Experimental Neurology, 181:115-119-129, 2003.*
Pettersson et al., Biodegradable fibrin conduit promotes long-term regeneration after peripheral nerve injury in adult rats, Journal of Plastic, Reconstructive & Aesthetic Surgery 63:1893e1899, 2010.*
Gao, Mingyong et al.: "*Templated agarose scaffolds for the support of motor axon regeneration into sites of complete spinal cord transection*", Biomaterials, Nov. 23, 2012, vol. 34, No. 5, doi: 10.1016/ J.Biomaterials.2012.10.070, ISSN 0142-9612, p. 1529-1536 1-14 p. W.
Kim, Howard et al.: "*Creating permissive microenvironments for stem cell transplantation into the central nervous system*"; Trends in Biotechnology, vol. 30, No. 1, doi: 10.1016/ J. Tibtech .2011.07. 002, ISSN 0167-7799, Aug. 9, 2011, p. 55-63 1-14 p. W.
Liu Y et al.: "*Transplants of fibroblasts genetically modified to express BDNF promote regeneration of adult rat rubrospinal axons and recovery of forelimb function.*", The Journal of Neuroscience : The Official Journal of The Society for Neuroscience Jun. 1, 1999, vol. 19, Nr. 11, p. 4370-4387, ISSN 1529-2401 1-14 p. 4371.
Lu, Paul et al: "*Long-Distance Growth and Connectivity of Neural Stem Cells after Severe Spinal Cord Injury*", Cell, Sep. 14, 2012, vol. 150, No. 6, doi:10.1016/J.Cell.2012.08.020, ISSN 0092-8674, p. 1264-1273 1-14 p. W.
Tetzlaff, Wolfram et al.: "*A Systematic Review of Cellular Transplantation Therapies for Spinal Cord Injury*", Journal of Neurotrauma, Aug. 1, 2011, vol. 28, No. 8, doi:10.1089/neu.2009. 1177, ISSN 0897-7151, p. 1611-1682 1-14 tab. 1,4,6,9 , p. 1651.
Xu, Liang et al.: "*Long-term fate of allogeneic neural stem cells following transplantation into injured spinal cord*"., Stem Cell Reviews Mar. 2010, vol. 6, Nr. 1, p. 121-136, ISSN 1558-6804 1-14 p. 127 , p. 121.
Yuan, Shauna H. et al.: "*Cell-Surface Marker Signatures for the Isolation of Neural Stem Cells, Glia and Neurons Derived from Human Pluripotent Stem Cells*"; vol. 6, No. 3, doi: 10.1371/Journal Pone.0017540, ISSN 1932-6203, Mar. 1, 2011, p. e17540.1-e17540. 16 1-14 p. A.
Extended European Search Report issued on Jun. 29, 2015 regarding EP12 85 7504.

* cited by examiner

*Primary Examiner* — Kimberly A. Ballard
*Assistant Examiner* — Stacey MacFarlane
(74) *Attorney, Agent, or Firm* — DLA Piper LLP (US)

(57) ABSTRACT

Methods for inducing non-embryonic lesioned central nervous system neurons to survive, integrate, extend axons over long distances, induce intra-lesion ingrowth of neurons into the lesion from host tissue and form synapses in vivo. Pluripotent neural stem cells are grafted into the lesioned CNS tissue within a tissue adhesive suspension, optionally in the presence of growth factors. No modification of the neuronal regenerative inhibitory environment of the CNS is necessary.

13 Claims, 18 Drawing Sheets

METHODS FOR USE OF NEURAL STEM CELL COMPOSITIONS FOR TREATMENT OF CENTRAL NERVOUS SYSTEM LESIONS

CROSS-REFERENCE TO RELATED APPLICATIONS

This application is a 35 USC §371 National Stage application of International Application No. PCT/US2012/068807 flied Dec. 10, 2012, which claims the benefit under 35 USC §119(c) to U.S. Application Ser. No. 61/569,564 filed Dec. 10, 2012. The disclosure of each of the prior applications is considered part of and is incorporated by reference in the disclosure of this application.

GRANT INFORMATION

This invention was made with government support under Grant No. R01 NS049881 awarded by the National institutes of Health. The government has certain rights in the invention.

BACKGROUND OF THE INVENTION

Field of the Invention

The invention relates to methods for treating central nervous system lesions in a mammal. The invention further relates to a method for using neural stem cells to induce formation of functional synaptic junctions and corticospinal regeneration in the spinal cord.

Background Information

The mammalian spinal cord shows little spontaneous recovery after injury. Furthermore, although regeneration of damaged spinal cord tissues (e.g., axons and neurons) can sometimes be induced to a degree through treatment, formation of functional synaptic junctions between axonal termini and adjacent neurons remains elusive.

The degree of motor function loss varies with the identity of the damaged tissue and the extent of damage incurred, as well as with species. For example, the rubrospinal tract influences movement through direct and reciprocal spinal motor projections that reflect activity of the rubro-cortico-cerebellar premotor pathway. The vestibulospinal and reticulospinal tracts affect postural control and balance during locomotion. Specialization in the vestibular system in particular has been important for the evolution of bipedal locomotion in humans. However, impairments in voluntary motor function after spinal cord injury in humans are most often attributed to disruption of corticospinal tract (CST) projections.

It has long been assumed that elicitation of long-distance axonal regeneration in the adult spinal cord would require modification of the inhibitory CNS milieu. Research over the last several decades has revealed numerous molecular mechanisms in the environment of the adult central nervous system (CNS) that contribute to the failure of axonal regeneration after injury. For example, myelin-associated proteins are released which inhibit axonal growth, inhibitory extracellular matrix molecules become deposited around injury sites, and positive environmental stimuli, such as growth factors, are absent.

The observation that at least some classes of adult CNS axons can grow over long distances in peripheral nerve bridges (but not within the CNS) supports the view that the adult CNS environment is inhibitory. However, some studies indicate that neuron-intrinsic mechanisms also contribute to axonal growth failure in the adult CNS. The extent to which therapies directed to modifying neuron-intrinsic mechanisms alone could overcome the inhibitory growth environment of the adult CNS is controversial. Conventional wisdom in the art, however, is that modification of the inhibitory environment is essential to correcting the neuronal damage and functional deficits which follow CNS injury (e.g., to the spinal cord).

To that end, various interventions have been considered to modify the inhibitory environment in the spinal cord, outside of a lesion site. Examples include immunosupression, administration of myelin-associated inhibitors (e.g., MAG and nogo) and/or targeting certain CNS receptors with, for example, acetylcholine or extracellular matrix molecules (e.g., laminin, immunoglobulins) and exposing the cord environment to neurotrophic factors.

To date, however, such interventions have failed to restore axonal growth and function to damaged, diseased or otherwise degenerated CNS neuronal populations. A need, therefore, exists for an effective therapy for CNS lesions.

SUMMARY OF THE INVENTION

The invention provides a method for treating a mammal which has suffered an lesion to its central nervous system (CNS), from injury, disease, degeneration or other damage. In a particular embodiment, the portion of the central nervous system to be treated is the spinal cord.

Surprisingly, the invention demonstrates that, contrary to conventional wisdom in the art, it is possible to achieve extensive, long-distance central nervous system axonal regeneration and formation of new synaptic junctions without additional manipulation of the cell growth inhibitory environment of the CNS. In this respect, despite the inhibitory milieu of the CNS, neuron-intrinsic mechanisms are sufficient to support remarkably extensive corticospinal regeneration and synapse formation after lesioning of the CNS, as in a spinal cord injury. However, engaging these mechanisms in a clinically successful manner requires specific handling of the neural stem cells for grafting into the CNS. The specific requirements for practice of a clinically useful protocol for grafting neural stem cells to the CNS are identified and provided by the invention.

According to the protocol, neural stem cells at an early, undifferentiated stage of development (N1 or earlier) are grafted to the site of one or more lesions for treatment within the central nervous system. Pluripotent neural stem cells derived from embryonic or adult nervous systems can be cultivated in vitro to an undifferentiated state capable of induced in vivo differentiation into neurons, astrocytes, and oligodendrocytes. The undifferentiated neural stem cells primarily applied according to the inventive protocol may optionally be enriched by addition of neural stem cells at a more differentiated stage of development. However, by themselves, post-natal neuronal cells cannot induce the extensive structural and functional recoveries provided according to the protocol of the invention.

For grafting into the lesion site, the neural stem cells are to be distributed evenly throughout the lesion to form a homogenous population of cells capable of forming relays across the lesion at different levels. A transplantation matrix, such as a fibrin glue, is therefore preferably used to maintain the cellular distribution within the lesion.

According to a further embodiment of the protocol, amplification of stem cell survival and axonal growth may be enhanced by supplying the neural stem cell graft with a growth factor source. For example, the source may be provided by co-administration or separate delivery of a growth factor, such as NT-3, BDNF, CTNF, NGF, NT-4/5, FGF, EGF and GDNF (including GDNF family neurotrophins such as neurturin). It will be appreciated that, in contrast to prior observations in the art, it will be sufficient to provide the growth factor source directly to the grafted cells at the treatment site(s). Applying growth factors to the CNS environment in which the lesion is situated to modify its inhibitory properties is not required.

In a particularly preferred embodiment, at least one growth factor is provided to the grafted neural stem cells. In another embodiment, a cocktail of growth factors are provided. A particularly preferred growth factor is BDNF to increase the number of growing axons and clustering of terminal axonal processes around host neuronal targets. Again, it will be appreciated that modification of the inhibitory environment in the CNS outside of the lesion (whether by growth factor administration or otherwise) is an optional step which, contrary to prior observations, is not necessary to induce axonal growth in the CNS according to the invention. Indeed, certain CNS environmental modifications, such as immunosuppression, may inhibit cell growth according to the invention.

Once prepared for implantation, the neural stem cells are implanted at the target lesion site according to the invention, suspended evenly in a transplantation matrix in the presence of at least one growth factor. Grafted neural stem cells differentiate, undergo axonal myelination, and establish synaptic contacts with host circuitry. Reciprocally, host axons penetrate grafts in the lesion site and establish putative synaptic contacts.

According to one embodiment, the lesion to be treated is in the spinal cord. Grafted neural stem cells neurons placed within a spinal cord lesion according to the invention readily propel axons beyond a lesion site over remarkably long distances through white matter tracts, as far as the brain and caudal half of the spinal cord.

The present invention therefore provides clinically useful methods to induce CNS neurons to survive, integrate, extend axons over very long distances and form synapses in the lesioned adult CNS.

DETAILED DESCRIPTION OF THE INVENTION

Preparation of Neural Stem Cell Grafts

Figure 1:
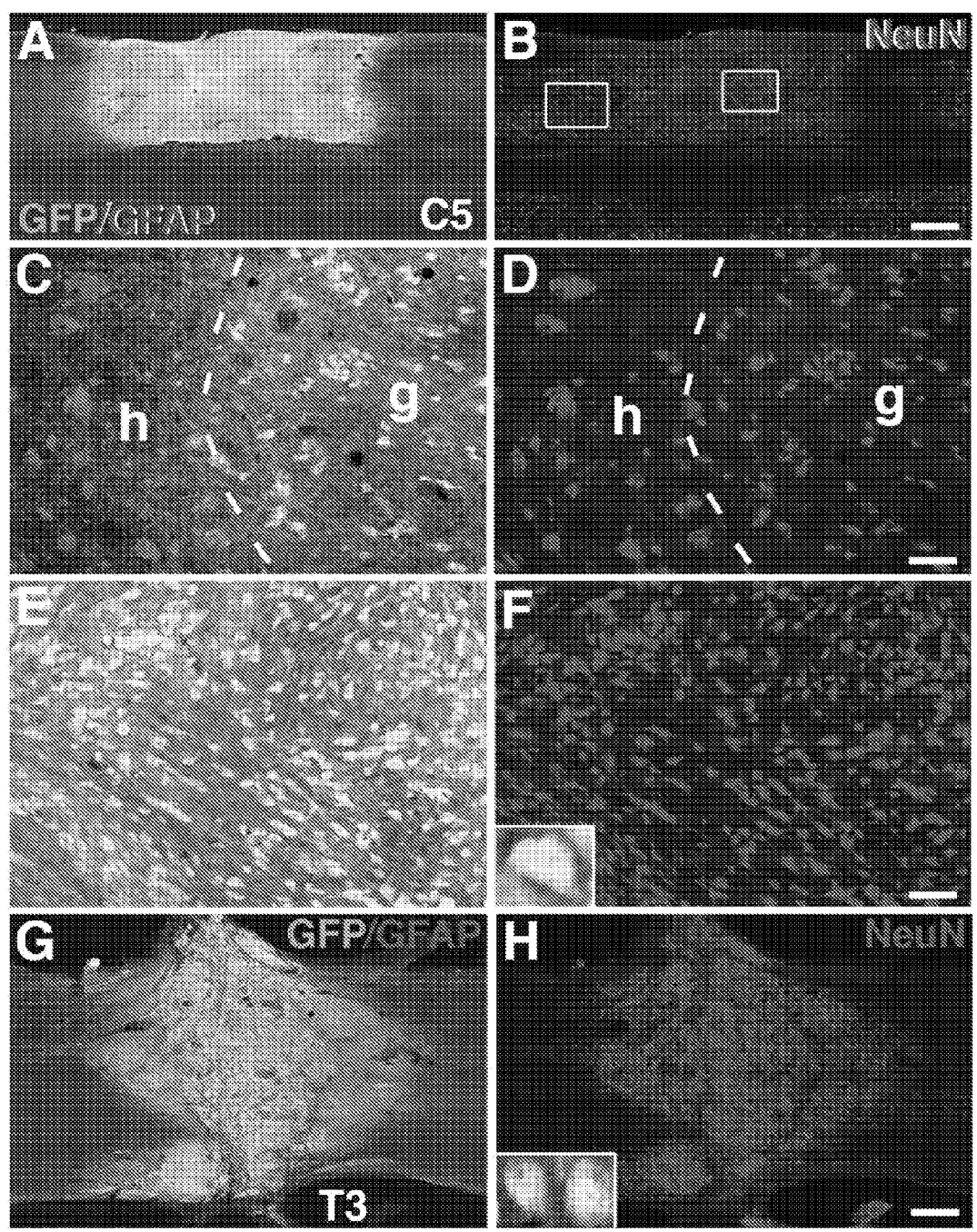
FIG. 1 (A-B) provides an overview of GFP (light regions), GFAP (dark regions) and NeuN (boxed regions) triple fluorescent immunolabeling of a horizontal section. As shown, the results demonstrate (A) excellent survival, integration and (B) differentiation/maturation of NeuN-positive neurons of E14 graft at C5 hemisection. (C-D) Higher magnification from left boxed area of panel B showing excellent integration and smooth transition from host neurons to grafted neurons. Dashed lines indicate graft (g)/host (h) interface. (E-F) Higher magnification of right boxed area from center of graft showing high density of NeuN-labeled neurons (inset). (G) GFP and GFAP double label shows excellent graft survival and integration into T3 complete transection site. (H) GFP and NeuN label in T3 complete transection site confirms extensive neuronal differentiation of grafted E14 spinal cord; co-localization shown in inset. Scale bar: A-B, 500 µm; C-D, 64 µm; E-F, 55 µm; G-H, 310 µm.

A neural stem cell is an undifferentiated neural cell that can be induced to proliferate. The neural stem cell is capable of self-maintenance, meaning that with each cell division, one daughter cell will also be a stem cell. The non-stem cell progeny of a neural stem cell are termed progenitor cells. The progenitor cells generated from a single multipotent neural stem cell are capable of differentiating into neurons, astrocytes (type I and type II) and oligodendrocytes. Hence, the neural stem cell is "pluripotent" because its progeny have multiple differentiative pathways.

The term "neural progenitor cell", as used herein, refers to an undifferentiated cell derived from a neural stem cell, and is not itself a stem cell. Some progenitor cells can produce progeny that are capable of differentiating into more than one cell type. A distinguishing feature of a progenitor cell is that, unlike a stem cell, it has limited proliferative ability and thus does not exhibit self-maintenance. It is committed to a particular path of differentiation and will, under appropriate conditions, eventually differentiate into glia or neurons.

For ease of reference, the phrase "neural stem cell" as used herein shall be understood to include, whenever appropriate, true stem cells as well as neural progenitor cells.

Pluripotent neural stem cells may be obtained from embryonic or adult neural tissue (for use to develop induced pluripotent cells) and cultured by means known in the art, briefly summarized for ease of reference hereinbelow. The neural tissue can be obtained from any animal that has neural tissue such as insects, fish, reptiles, birds, amphibians, mammals and the like. The preferred source neural tissue is from mammals, preferably rodents and primates, and most preferably, mice and humans.

Cells can be obtained from donor tissue by dissociation of individual cells from the connecting extracellular matrix of the tissue. Dissociation of fetal cells can be carried out in tissue culture medium, while a preferable medium for dissociation of juvenile and adult cells is low $Ca^{2+}$ artificial cerebral spinal fluid (aCSF). The neural cells can be cultured in suspension or on a fixed substrate. However, substrates tend to induce differentiation of the neural stem cell progeny. Thus, suspension cultures are preferred if large numbers of undifferentiated neural stem cell progeny are desired.

Neural crest stem cells which ordinarily differentiate into peripheral nervous system cells (not functional in the CNS) may also be isolated from multiple peripheral organs and maintained in neurosphere culture. When transplanted into the embryonic or adult CNS, they can differentiate predominantly into cells of the oligodendrocyte lineage (Binder, et al., *J. Neurosci.*, 31:6379-6391 (2011)).

Dissociated neural stem cells can be placed into any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like.

However, a preferred embodiment for proliferation of neural stem cells is to use a defined, serum-free culture medium, as serum tends to induce differentiation and contains unknown components. A relatively simple way to reconstitute neural commitment in vitro and achieve efficient neuronal production relies upon monolayer differentiation of ES cells is provided by a method developed by Ying, et al. (Ying, et al., *Nat. Biotechnol.*, 21: 183-186, 2003, incorporated herein by this reference). In this method, embryonic cells are cultured in defined serum- and feeder-free conditions in the absence of BMP signals that are known to inhibit neural fate. In these conditions, ES cells undergo neural commitment through an autocrine induction mechanism, where FGF signalling plays a pivotal role, as it does in the embryo. This method results in an efficient neural commitment and differentiation. Additional suitable culturing methods for production of neural stem cells will be known or readily ascertainable to those of ordinary skill in the art.

Neural stem cells may also be obtained through cell banks, such as the Human Neural Stem Cell Resource (www.hnscr.org), the New York Neural Stem Cell Institute (www.nstemcell.org) and commercial sources such as Life Technologies, Inc., Carlsbad, Calif.

Figure 14:
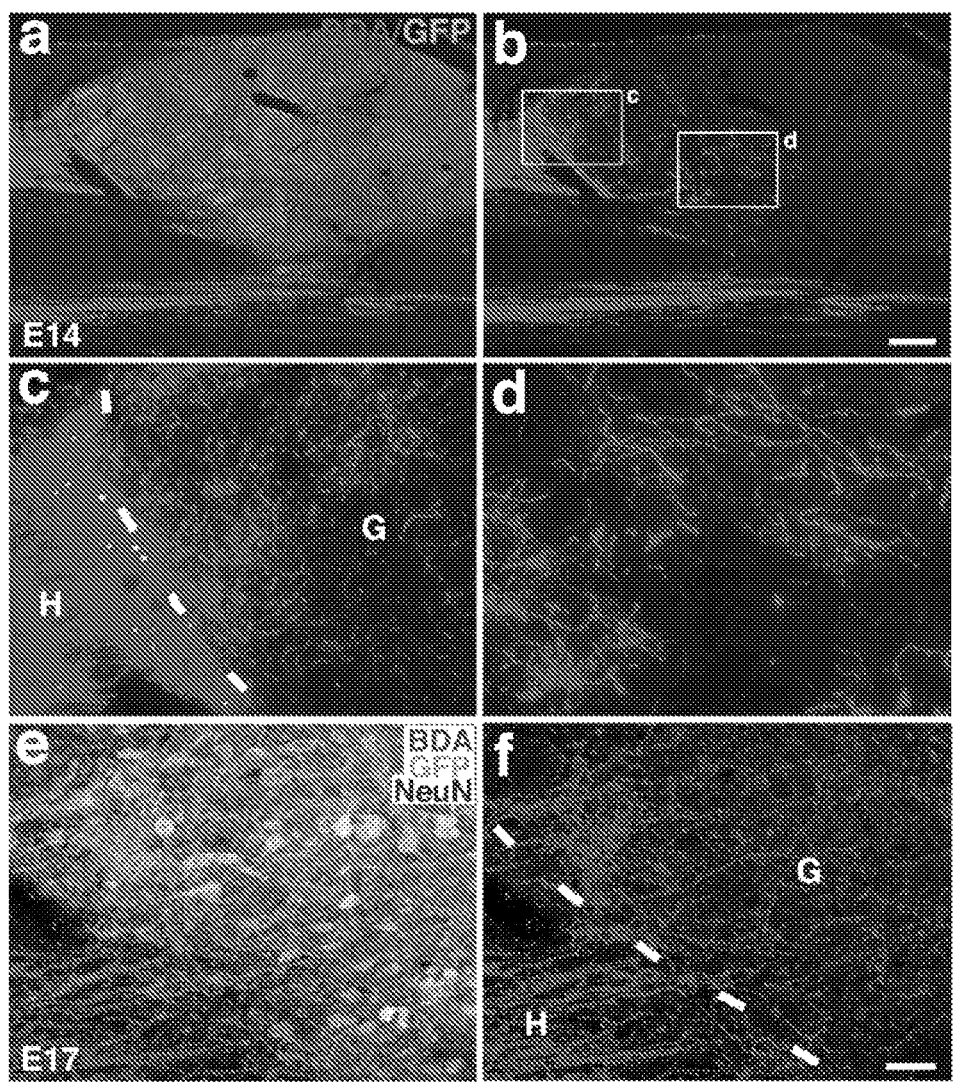
FIG. 14 shows (A) GFP, GFAP and NeuN triple labeling reveals survival of grafted postnatal day 1 neural cells (GFP) with fibrin and growth factor cocktails in the lesion site. Lesion is outlined by GFAP. Two month survival. (B) Higher magnification demonstrates that grafted cells survive in the center of the lesion site, and some cells are GFAP positive. However, there are no cells that label for NeuN, indicating lack of neuronal differentiation. (C) Grafted cells show only short extension of processes into host, in distinct contrast to cells that are grafted at earlier stages of the neural stem cell state. Scale bar: a, 300 µm; b-c 62 µm.
Figure 15:
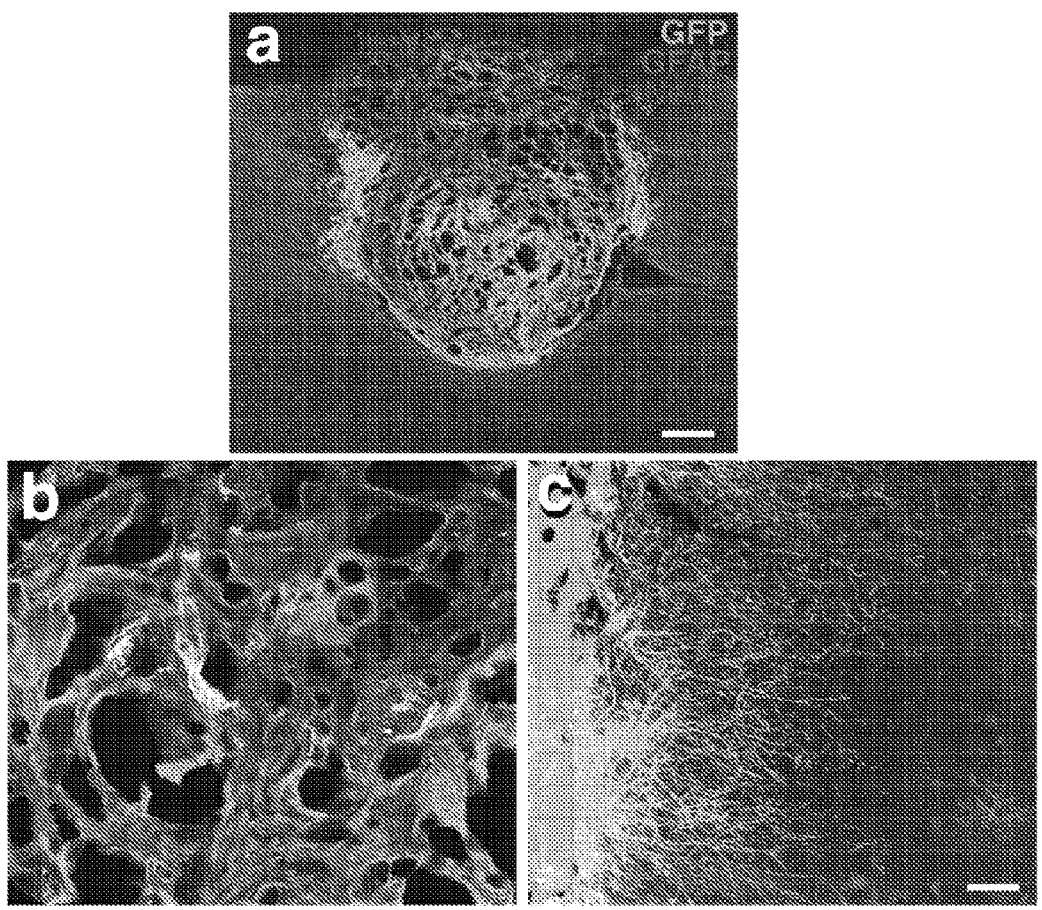
FIG. 15 shows (A) GFP, GFAP and NeuN triple labeling reveals poor survival of grafted adult neural cells (GFP) with fibrin and growth factor cocktails in the lesion site outlined by GFAP. Two month survival time after spinal cord injury. (B) Higher magnification demonstrates that surviving grafted cells are sometimes GFP positive, but NeuN negative. (C) Grafted cells have short processes extending into host. Scale bar: a, 300 µm; b-c 62 µm.

The stage of development achieved by the neural stem cells is of particular significance for use in the protocol of the invention. As illustrated in FIGS. 14 and 15, post-natal day one neural cells and adult neural cells do not differentiate into neurons (although they may produce glia) and do not form lengthy extensions into host tissue, in distinct contrast to cells that are grafted at earlier stages of neural stem cell development. Further, the survival of lesion-grafted adult neural cells is inadequate for use in the inventive protocol.

In general, neural stem cells differentiate through N1, an initiation stage; N2, a neural progenitor cell (NPC) stage that produces only neurons upon further differentiation; and N3, which produces both neurons and glial cells. These stages of differentiation are characterized by expression of different genes which can be used as markers for cells to be grafted being at a stage appropriate for use in the invention (see, e.g., Wu, et al., *PNAS USA*, 527(11): 5254-5259 (2010)).

In contrast to earlier assumptions, only fully pluripotent (N1 stage or earlier) cells are effective to achieve the goals of the invention; i.e., axonal growth, formation of new functional synapse, and induction of in-growth into the lesion site from unlesioned areas of the CNS (e.g., neuronal populations of the spinal cord communicating with the lesion site). Stem cells and progenitor cells differentitated to be fate-specific for only neurons and/or astrocytes and/or oligodendrocytes at the time of implantation will lose effectiveness. While pluripotent neural stem cells used in the invention may be supplemented by such cells at later stages of differentiation if clinically desired, the primary protocol requires use of N1 stage, undifferentiated cells. Thus, for purposes of this disclosure, "neural stem cells" shall be understood to refer to such undifferentiated cells unless context otherwise requires.

For use in humans, cells having phenotypic characteristics of human neural stem cells will be preferred. In general, undifferentiated human embryonic stem cells will express all human embryonic surface antigens (e.g., TRA-1-60/81 and SSEA4) as well as transcription factors OCT4 and SOX2. The N1 initiation stage cells for principal use according to the inventive protocol do not maintain TRA-1-60/81 expression but may experience lower levels of SSEA4 expression. Expression of SSEA1 and OCT4 may also be detectable.

In contrast, N2 cells may lose OCT4 as well as SSEA4 expression, but have detectable levels of NESTIN, PAX6, and SOX1 expression, as well as neuronal stem/precursor markers MUSASHI. Glial fibrillary acidic protein (GFAP) may not be expressed. Upon withdrawal of growth factors, N2 cells will predominantly differentiate into neurons rather than glial cells, as indicated by the expression of neuronal marker TUE. N3 stage cells exhibit GFAP expression. After bFGF/EGF withdrawal, more glial cells than neurons are generated from N3 stage cells. These gene expression patterns may be leveraged for detection of the expressed proteins as markers for the various stages of development.

For preparation of the primary cell graft, pluripotent neural stem cells are to be provided by even distribution throughout in a transplantation matrix before grafting to ensure even distribution of cells, growing axons and new synaptic junctions within and from the lesion to be treated. Transplantation matrices suitable for use in the body are known; for example, the tissue adhesive compositions described by Petersen, et al., *Gastrointestinal Endoscopy*, 60(3):327-333 (2004). However, a mixture of fibrin and thrombin is particularly well-suited for use in the invention. Such mixtures are commercially available as fibrin glue products; e.g., a 50:50 mixture product from Sigma Chemicals. For use in the graft, neural stem cells are evenly suspended in the tissue adhesive, preferably just prior to implantation.

The cell/adhesive suspension is preferably supplemented with at least one growth factor. As used herein, the term "growth factor" refers to a protein, peptide or other molecule having a growth, proliferative, differentiative, or trophic effect on neural stem cells and/or neural stem cell progeny. Growth factors which may be used for inducing proliferation include any trophic factor that allows neural stem cells and precursor cells to proliferate, including any molecule which binds to a receptor on the surface of the cell to exert a trophic, or growth-inducing effect on the cell. Among the growth factors and other molecules that can be used to influence the differentiation of precursor cells in vitro are FGF-1, FGF-2, ciliary neurotrophic factor (CNTF), NGF, brain-derived neurotrophic factor (BDNF), neurotrophin 3, neurotrophin 4, interleukins, leukemia inhibitory factor (LIF), GDNF family receptor ligands, cyclic adenosine monophosphate, forskolin, tetanus toxin, high levels of potassium, amphiregulin, TGF-.alpha., TGF-.beta., insulin-like growth factors, dexamethasone (glucocorticoid hormone), isobutyl 3-methylxanthine, somatostatin, growth hormone, retinoic acid, and PDGF.

Preferred proliferation-inducing growth factors include BNDF, EGF and FGF-1 or FGF-2. Growth factors are usually added to the culture medium at concentrations ranging between about 1 fg/ml of a pharmaceutically acceptable composition (including, for example, CNS compatible carriers, excipients and/or buffers) to 1 mg/ml. Concentrations between about 1 to 100 ng/ml are usually sufficient and may be conveniently added to the cell graft composition, co-administered into the graft and/or administered within diffusion distance of the graft as described hereinbelow. Simple titration experiments can be easily performed to determine the optimal concentration of a particular growth factor.

In a particularly preferred approach, the growth factors are provided by simple mixture of the proteins with the neural stem cell/transplantation matrix composition. Human growth factors are preferred for use in therapy of human disease according to the invention due to their relatively low immunogenicity as compared to allogenic growth factors. However, growth factors of other species (e.g., non-human primates) are known which may also be suitable for use in the invention with adequate testing of the kind described herein.

Growth factors may also be provided by expression from a co-administered recombinant expression vector or from donor cells. Coding polynucleotides, precursors and promoters for a number of human nervous system growth factors are known, as are coding sequences for nervous system growth factors of other mammalian species. For example, GenBank M61176 sets forth the coding sequence (mRNA) for BDNF; BDNF precursor is set forth at BF439589; and a BDNF specific promoter is set forth at E05933. A similar range of coding sequences for other nervous system growth factors are also available through GenBank and other publicly accessible nucleotide sequence databases.

Suitable recombinant expression vectors (especially ones able to transfect and be expressed in non-dividing cells) include DNA viruses such as adenoviruses, adeno-associated virus (AAV), and certain RNA viruses such as HIV-based lentiviruses, feline immunodeficiency virus (FIV) and equine immunodeficiency virus (EIV). Other vectors capable of transfecting and being expressed within non-dividing cells include herpes simplex virus (HSV). For further review, those of ordinary skill may wish to consult Maniatis et al., in *Molecular Cloning: A Laboratory Manual* (Cold Spring Harbor Laboratory, 1982) and Alto, et al., *Nat. Neurosci.*, 12, 1106-1113 (2009) (AAV2-BDNF)). Concerning retrovirus construction in particular, see, e.g., Kriegler, *Gene Transfer and Expression, A Laboratory Manual*, (W. Freeman Co., 1990) and Murray, E J, ed., *Methods in Molecular Biology*, Vol. 7, (Humana Press, 1991).

Preparation of growth factor-expressing donor cells (e.g., fibroblasts) may be as described in Tuszynski, U.S. Pat. No. 6,451,306. Such cells may be co-grafted into a lesion with the neural stem cells of the invention, but need not be included within the neural stem cell/transplantation matrix composition.

Neural stem cells can be used for transplantation into a heterologous, autologous, or xenogeneic host. The neural stem cell progeny can be administered to any animal with abnormal neurological or neurodegenerative symptoms obtained in any manner, including those obtained as a:result of mechanical, chemical, or electrolytic lesions, as a result of experimental aspiration of neural areas, or as a result of aging processes. Particularly preferable lesions in non-human animal models (e.g., rats) are obtained with 6-hydroxy-dopamine (6-OHDA), 1-methyl-4-phenyl-1,2,3,6 tetrahydropyridine (MPTP), ibotenic acid and the like.

Neural Stem Cell Grafting

The invention provides a method for differentiation of grafted neural stem cells in vivo without need for intervention to modify the inhibitory environment of the CNS. As such, the usual requirements for co-administration of a growth factor into the spinal cord at a distance from the lesion site, or pharmaceutical composition to block the inhibitory influence and/or stimulate neural stem cells and stem cell progeny to proliferate and ultimately differentiate, may be dispensed with in practice of the invention.

For grafting, neural stem cells are delivered throughout any affected neural area (e.g., up to filling a lesion to its borders) using any method which maintains the integrity of surrounding areas of the treatment site, preferably by injection cannula. Suitable injection methods for use in the spinal cord include those described in the examples herein as well as in Tuszynski, U.S. Pat. No. 6,167,888. Additional approaches and methods for cell transplantation may be found in *Neural Grafting in the Mammalian CNS*, Bjorklund and Stenevi, eds., (Elsevier Science, 1985).

Cells, growth factors and transplantation matrix may be co-administered; e.g., by injection concurrently as a mixed suspension into the lesion site using rapid continuous infusion. Alternatively, the growth factors may be administered separately within, or within diffusion distance of, the lesion (e.g., 1 mm from its borders in the rat, where equivalent distances can be readily extrapolated for other species). Care must be taken to avoid inclusion of air pockets in the lesion site, which would otherwise result in acellular regions that undermine the effectiveness of the invention. Ultrasound guidance to allow full visualization and confirm filling of the lesion site is useful but not essential.

Neural stem cell concentration in the grafting mixture can range from 10,000 to 500,000 cells per microliter of the transplantation matrix, including 12,000 to 450,000 cells/μl, 15,000 to 425,000 cells/μl, 20,000 to 400,000 cells/μl, and so on for all concentrations thereinbetween, with the selection of a particular concentration to be made in the clinical judgment of a treating physician. It is not necessary and, while optional at the clinician's judgment, may be counter to efficacy to distribute neural stem cells directly into non-lesioned regions of the host spinal cord. The lesion site is ideally to be filled with the transplantation matrix through the full ventral to dorsal, and medial to lateral, extent of the lesion.

Post-Treatment Monitoring

Survival of the graft in the living host can be examined using various non-invasive scans such as computerized axial tomography (CAT scan or CT scan), nuclear magnetic resonance or magnetic resonance imaging (NMR or MRI) or more preferably positron emission tomography (PET) scans.

Post-mortem examination of graft survival can be done by removing the neural tissue, and examining the affected region macroscopically, or more preferably using microscopy. Cells can be stained with any stains visible under light or electron microscopic conditions, more particularly with stains which are specific for neurons and glia. Differentiation in vivo of grafted neural stem cells may be monitored by, for example, immunocytochemistry to detect immunoreactivity for NSE, NF, NeuN, and the neuron specific protein, tau-1.

Type I astrocytes, which are differentiated glial cells that have a flat, protoplasmic/fibroblast-like morphology, are preferably identified by their immunoreactivity for GFAP but not A2B5. Type II astrocytes, which are differentiated glial cells that display a stellate process-bearing morphology, are preferably identified using immunocytochemistry by their phenotype GFAP(+), A2B5(+) phenotype.

Cells that do not express intermediate filaments specific for neurons or for astrocytes, begin to express markers specific for oligodendrocytes in a correct temporal fashion. That is, the cells first become immunoreactive for O4, galactocerebroside (GalC, a myelin glycolipid) and finally, MBP. These cells also possess a characteristic oligodendrocyte morphology.

Neurons can also be identified based on their specific neurotransmitter phenotype. For example, antibodies can be used in in vitro immunohistochemistry that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or anti-diuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β-endorphin and enkephalins such as met- and leu-enkephalin, prostaglandins, amino acids such as gamma-amino butyric acid (GABA), glycine, glutamate, cysteine, taurine and aspartate and dipeptides such as carnosine. Antibodies to neurotransmitter-synthesizing enzymes can also be used such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors and the dopamine receptors. In situ hybridization histochemistry can also be performed, using cDNA or RNA probes specific for the peptide neurotransmitter or the neurotransmitter synthesizing enzyme mRNAs.

Functional integration of the graft into the host's neural tissue can be assessed by examining the effectiveness of grafts on restoring various functions, including but not limited to tests for motor, sensory, autonomic, endocrine, and possibly cognitive functions. Motor tests which can be used include those which quantitate use of the limbs for motor tasks such as locomotion and food retrieval, accuracy of limb placement in walking over a grid, and walking on a treadmill. Sensory tasks include measures of thermal sensitivity and allodynia, including von Frey hair analysis. Autonomic outcomes are measured using assessment of heart rate, blood pressure and reflex responses to stimuli. Cognitive tests include various tests of ability to perform everyday tasks, as well as various memory tests, including maze performance.

Animal Models

The animal model described in the examples demonstrates the efficacy of the inventive method. Additional animal models for CNS lesioning are known in the art and have been described in, for example, Akhtar, et al., *Reviews in the Neurosciences*, 19:47-60 (2008), and Onifer, et al., *Inst. Lab. Anim. Res.* 48(2) 2007.

The invention having been fully described, those of ordinary skill in the art may recognize modifications and extensions to the invention. All such modifications and extensions are considered to be within the scope of the invention.

EXAMPLE I

Animal Model of Spinal Cord Injury

Adult female Fischer 344 rats (160-200 g, n=27) were subjects of this study. NIH guidelines for laboratory animal care and safety were strictly followed. Animals had free access to food and water throughout the study. All surgery was done under deep anesthesia using a combination (2 ml/kg) of ketamine (25 mg/ml), xylazine (1.3 gm/ml) and acepromazine (0.25 mg/ml). Adult female Fischer 344 rats underwent C5 lateral hemisection or T3 complete transection.

EXAMPLE II

Preparation of Embryonic Cell Grafts

Embryonic day 14 (E14) spinal cord from transgenic Fischer 344-Tg (EGFP) rats ubiquitously express GFP under the ubiquitin C promoter and provided donor tissue for grafting (Rat Resource and Research Center, University of Missouri, Columbia, Mo.). Following C5 or T3 dorsal laminectomy, the dura was cut longitudinally and retracted. A 2-mm-long block of spinal cord was cut and removed using a combination of iridectomy scissors and microaspiration, with visual verification to ensure complete transection ventrally and laterally. E14 spinal cord from Fischer 344 rats expressing GFP was freshly dissected and dissociated.

Dissociated E14 cells were re-suspended in a fibrin matrix (25 mg/ml fibrinogen and 25 U/ml thrombin). Growth factors were added to the cell/adhesive suspension: BDNF (50 µg/ml), neurotrophin-3 (NT-3; 50 µg/ml), platelet-derived growth factor (PDGF-AA; 10 µg/ml), insulin-like growth factor 1 (IGF-1; 10 µg/ml), epidermal growth factor (EGF; 10 µg/ml), basic fibroblast growth factor (bFGF; 10 µg/ml), glial cell line-derived neurotrophic factor (GDNF; 10 µg/ml), hepatocyte growth factor (HGF; 10 µg/ml), fibroblast factor (aFGF; 10 µg/ml) and calpain inhibitor (MDL28170; 50 µM)

EXAMPLE III

Grafting of Pluripotent Neural Stem Cells Derived from Embryonic Spinal Cord Spinal cord tissue derived from genetically modified green fluorescent protein (GFP)—expressing rat embryos was grafted to the adult lesioned spinal cord. Under the ubiquitin C promoter, "green" rats express the GFP reporter gene in every cell, providing an unprecedented opportunity to track the fate, integration, extension and differentiation of grafted cells types within the inhibitory milieu of the adult injured spinal cord.

Cell suspensions of embryonic day 14 (E14) spinal cords from Fischer 344 rats expressing GFP under the ubiquitin C promoter were grafted into either acute mid-cervical (C5) lateral hemisection lesion sites or, two weeks after injury, into upper thoracic (T3) complete transection lesion sites, in non-transgenic F344 rats.

16 adult rats underwent C5 hemisection lesions and were divided into two groups. One group of 6 rats received E14 GFP-expressing grafts only (n=6), while a second group of 10 rats received E14 GFP-expressing grafts together with adeno-associated virus-serotype 2 (AAV2) vectors expressing BDNF (AAV2-BDNF; Alto, et al., Nat. Neurosci., 12, 1106-1113 (2009)) injected into host gray matter 1 mm rostral and caudal to the lesion (n=10). Additionally, 11 adult wild-type rats underwent T3 complete transections: 8 received E14 GFP-expressing grafts to the lesion site (without AAV2-BDNF injections), while the three remaining subjects served as ungrafted, lesioned controls.

For C5 hemisection lesions, 5 µl of dissociated cells were immediately micro-injected into the lesion cavity (n=16). The dura was closed to retain cells in the lesion site and covered with agarose film and fibrin (Baxter, Deerfield, Ill.). In the C5 transplant group (n=16), 10 subjects also received in vivo BDNF gene delivery by injecting 2 µl of AAV2-BDNF ($1 \times 10^{12}$ genomic particles per ml, Gene Therapy Center, University of North Carolina at Chapel Hill), 1 mm rostral and 1 mm caudal to the lesion site at coordinates ML 0.8 mm and DV 1.5 mm using a pulled glass micropipette with an inner diameter of 40 µm, connected to a PicoSpritzer II (General Valve, Fairfield, N.J.). AAV2 vectors were self-complimentary. For subjects with T3 complete transections (n=11), 10 µl of the E14 GFP-expressing cells were micro-injected into the lesion cavity 2 weeks after the injury (N=8). Controls underwent lesions alone (N=3).

Subjects with C5 hemisections survived for 3 months, and T3 complete transections survived 6 weeks post-grafting.

EXAMPLE IV

Post-Mortem Analysis of Treated Animals

Two weeks before post-mortem analysis, reticulospinal tract axons in treated animals were anterogradely labeled by injection of 0.5 µl of 10% biotinylated dextran amine (BDA; MW 10,000, Molecular Probes) into each of four sites spanning the right gigantocellular reticular nucleus (bregma, 11-12.5 mm; lateral, 8 mm; depth, 8.2-7.3 mm) in subjects with C5 hemisection.

For post-mortem analysis, animals were perfused with 2% paraformaldehyde and 0.2% para benzoquinone in 0.1 M phosphate buffer (pH 7.2). Spinal cords were dissected, post-fixed overnight at 4° C. and then transferred to 30% sucrose for 72 hours. 1.5 mm-long horizontal sections of spinal cords containing the lesion/transplant site were sectioned on a cryostat set at 30 µm thickness. Coronal sections from the spinal cord rostral to (C2) and caudal to the lesion/transplant site at upper thoracic (T1), middle thoracic (T8) and lumbar enlargement (L4) were also examined. In addition, cerebral cortex, thalamus, brainstem, and ventral/dorsal roots adjacent to embryonic grafts were examined for GFP labeling.

Immunohistochemistry was performed to assess survival, maturation, integration and outgrowth of grafted neurons. Free-floating sections were incubated with primary antibodies against jellyfish green fluorescent protein (GFP; rabbit, Invitrogen @ 1:1,500 or goat from Chemicon @ 1:1500 to label GFP-expressing E14 spinal cord transplants); GFAP (mouse, Chemicon @ 1:1500 or rabbit, Dako at @ 1:1500 to label astrocytes); BDNF (Amgen, rabbit at @ 1:1000 to label BDNF expression); NeuN (mouse from Chemicon @ 1:200 to label mature neurons); choline acetyltransferase (ChAT; goat from Chemicon @ 1:200 to label spinal cord motor neurons and motor axons); MAP-2 (mouse from Chemicon @ 1:10,000 to label mature neurons); BIII tubulin (mouse from Chemicon @ 1:500 to label immature and mature neurons), neurofilament (NF; mouse from Chemicon @ 1:1500 to label axons); calcitonin gene-related peptide (CGRP; rabbit from Chemicon @ 1:5000 to label primary sensory axons); myelin-associated glycoprotein (MAG; mouse from Chemicon @ 1:200 to label myelin); glutamic acid decarboxylase 65 or 67 (GAD65, goat from RD System, or GAD67, mouse from Millipore @1:1000 to label neurotransmitter); vesicular glutamate transporters 1/2 (vGlut1/2, mouse from Chemicon @1:1000 to label neurotransmitter); synasptophysin (mouse from Chemicon @ 1:1000 to label synapse), Adenomatous Ployposis Coli (APC, monoclonal antibody from Oncogene @ 1:400 to label oligodendrocytes), nestin (monoclonal antibody from Chemicon @ 1:400 to label neuroepithelial stem cells); chondroitin sulfate proteoglycan (CS56, monoclonal from Sigma @ 1:200).

Sections were incubated overnight at 4° C., then incubated in Alexa 488, 594 or 647 conjugated goat or donkey secondary antibodies (1:250, Invitrogen) for 2.5 hr at room temperature. For nuclear staining, 4&,6-diamidino-2-phenylindole (DAPI) (200 ng/ml) was added to the final wash. BDA-labeled reticulospinal tract axons were detected by double fluorescent labeling with GFP. After blocking with 5% donkey serum, every $6^{th}$ section was incubated with primary antibody directed against GFP (rabbit) and Alexa 594-conjugated streptavidin (to bind to BDA-labeled reticulospinal tract axons) overnight at 4° C. After washes, sections were incubated with Alexa 488 conjugated donkey anti-rabbit secondary antibodies for 2.5 hr at room temperature.

For examination and quantification of GFP-labeled neurites, light level GFP immunolabeling was performed in every sixth section incubated overnight at 4° C. with GFP primary antibody (rabbit at 1:3000) and then with horseradish peroxidase (HRP) conjugated secondary antibodies (1:50, Vector Laboratory, Burlingame, Calif.) for 1 hr at room temperature. Diaminobenzidine (0.05%) with nickel chloride (0.04%) were used as chromagens, with reactions sustained for 10 min at room temperature.

Cellular differentiation was determined by counting individual cells labeled for NeuN, GFAP or APC within a fixed box size of 1600×1200 pixels at 400× magnification within the graft, divided by the total number of cells per sample box labeled with DAPI. Two randomly selected fields corresponding to the graft epicenter were counted in each subject for each label, and all analyses were conducted in a blinded manner. The number of ChAT- and GAD67-immunolabeled transplanted embryonic neurons was sampled in every $6^{th}$ section immunolabeled for ChAT and GAD67 (both labels were performed in the same section) using an Olympus fluorescent microscope at 400× magnification. The number of ChAT-labeled motor neurons or GAD67 inhibitory neurons co-localized with GFP was counted in each section and multiplied by the sampling fraction (6). GFP axon number was quantified in every $6^{th}$ section both rostral and caudal to the lesion/graft. Lesion margins were determined using GFAP and GFP double fluorescent immunolabeling, and axons crossing a vertical line in horizontal sections 1, 3, and 5 mm rostral and caudal to the lesion/graft border were counted. Total neurite number/subject was calculated by multiplying by the sampling proportion (1-in-6). Observers were blinded to group identity.

GFP terminal bouton density was quantified 1 mm caudal to the lesion/graft site. 32 BDNF-expressing neurons and 31 non-BDNF-expressing neurons were sampled per group at 400× magnification. High resolution confocal images were analyzed using ImageJ, and the area of neuronal soma and the proportion of the field (measured in pixels) occupied by GFP reaction product in terminal bouton surrounding the neuronal soma was quantified. GFP terminal bouton density was expressed as (GFP-labeled pixels)/(neuronal somal area).

The penetration of BDA-labeled reticulospinal axons into embryonic grafts was quantified using NIH Image J software analysis. The margins of the lesion and graft were determined by GFP labeling, then two randomly selected fields within each graft in the lesion site were measured in two separate sections from each subject. The number of pixels occupied by BDA-labeled axons within a fixed box size of 1600×12000 pixels at 400× magnification was measured (E-14 graft alone, n=6 animal; E14-BDNF animals, n=10). Threshold values on video images were chosen such that only immunolabeled axons were measured, and nonspecific background labeling was not detected. Axonal density within embryonic grafts was expressed as total labeled pixels per unit area (1600×1200 pixels).

Electron microscopic analysis of synapse formation and myelination was performed. Briefly, two rats with T3 complete transections that received E14 embryonic grafts were perfused with 4% paraformaldehyde plus 0.25% glutaraldehyde (survival time three months), and spinal cord parenchyma 2 mm caudal to the lesion/graft site was sectioned in the coronal plane, then immunolabeled for GFP with Diaminobenzidine (DAB) and nickel chloride. Sections were then post-fixed with 1% osmium tetroxide, dehydrated, embedded in Durcupan resin, and sectioned at 60 nm thickness. Individual GFP-labeled axons or axonal terminals were located and assessed using a FEI 200 KV Sphera microcope at the UCSD CryoElectron Microscopy Facility.

The BBB open field 21-point locomotion rating scale was assessed on days 1, 7, and 14 post-lesion, then weekly thereafter by two independent observers blinded to group identity.

In all quantification procedures, observers were blinded to the nature of the experimental manipulation. Multiple group comparisons were made using one-way analysis of variance (ANOVA; JMP software) at a designated significance level of 95%. Two-group comparisons were tested by Student's t-test. Data are presented herein and in the accompanying Figures as mean±SEM.

EXAMPLE V

Figure 9:
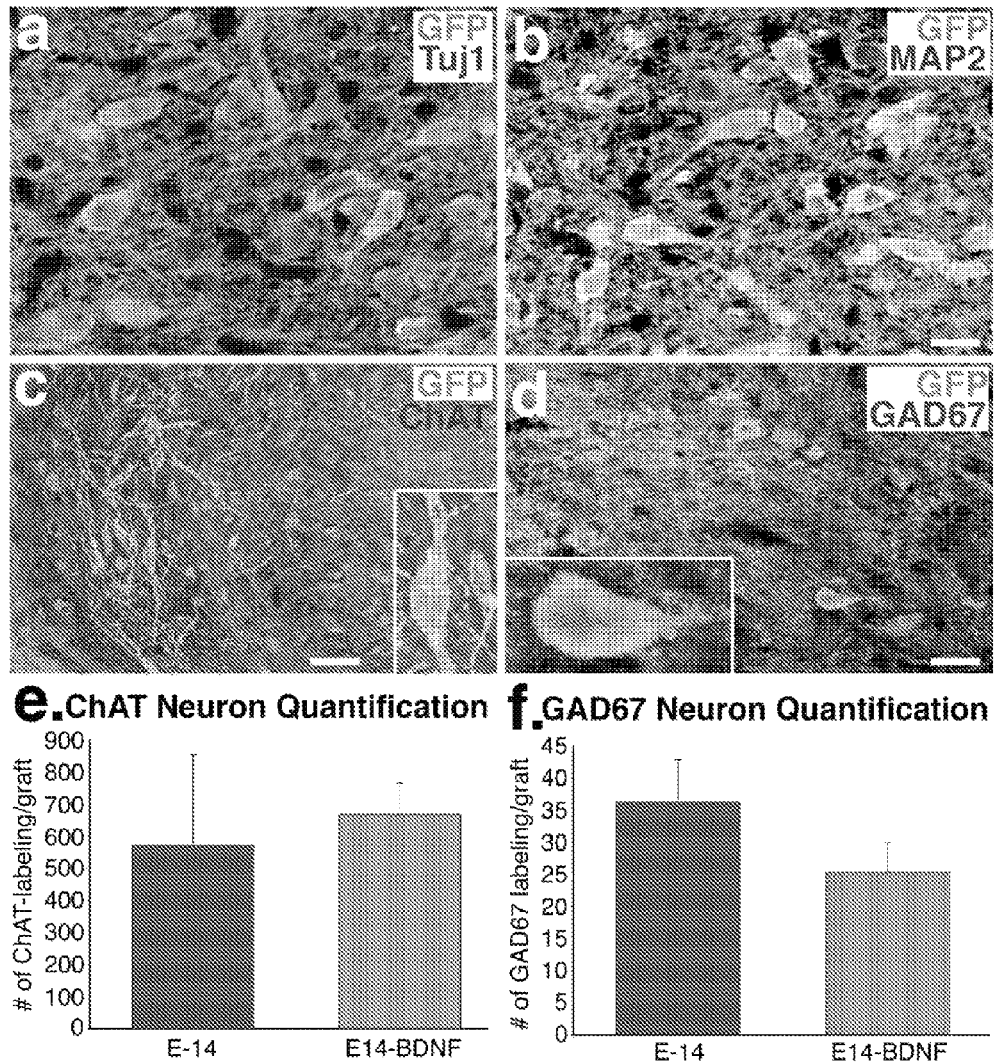
FIG. 9 shows Immunocytochemistry reveals co-localization of large GFP-expressing grafted cells with the neuronal markers (A) Tuj1 (βIII tubulin) and (B) MAP2. Some GFP-labeled cells also co-localize with (C) the motor neuronal marker ChAT and (D) the inhibitory neuronal marker GAD67. (E-F) Quantification of ChAT- and GAD67-expressing cells numbers within embryonic grafts. Co-injection of AAV2 vectors expressing BDNF into host spinal cord does not significantly alter the number of neurons expressing ChAT (p=0.75, Student's t test) or GAD67 (p=0.14, Student's t test). Scale bar: A-B, 16 µm; C, 28 µm; D, 48 µm.
Figure 10:
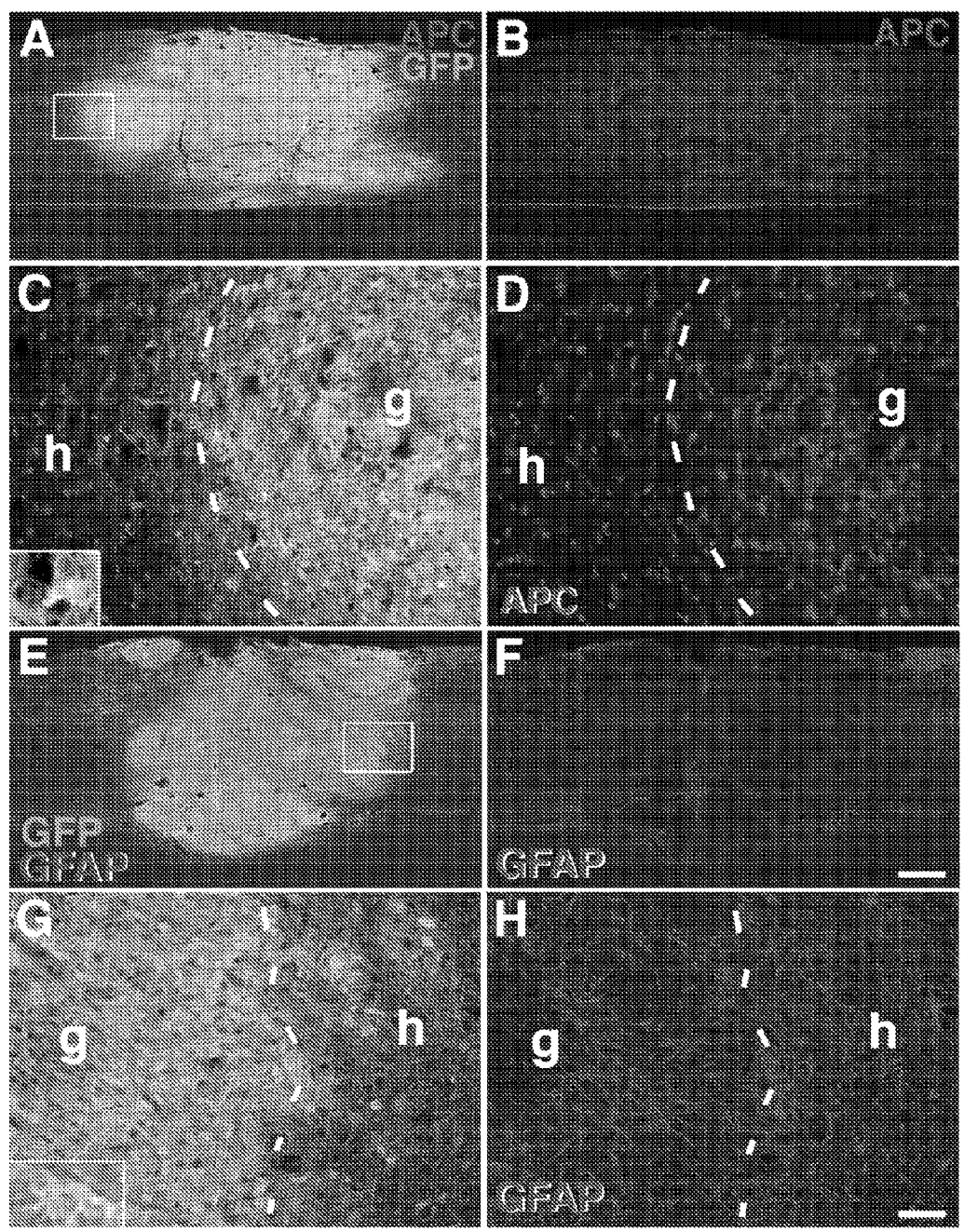
FIG. 10 shows (A-B) GFP and APC double fluorescent immunolabeling reveals co-localization of some grafted GFP-expressing E14 cells with the oligodendrocyte marker APC. (C-D) Higher magnification views from boxed area of panel A shows excellent graft integration within host lesion site, and seamless transition from host oligodendrocyte labeling (left of dashed line) to graft oligodendrocyte labeling (right of dashed line). (E-F) GFP and GFAP immunolabeling reveals co-localization of grafted GFP-expressing E14 cells with the astrocyte marker GFAP. (G-H) Higher magnification views from boxed area of panel E also demonstrate excellent graft integration into lesion site. Scale bar: A-B, E-F, 400 µm; C-D, G-H, 64 µm.
Figure 11:
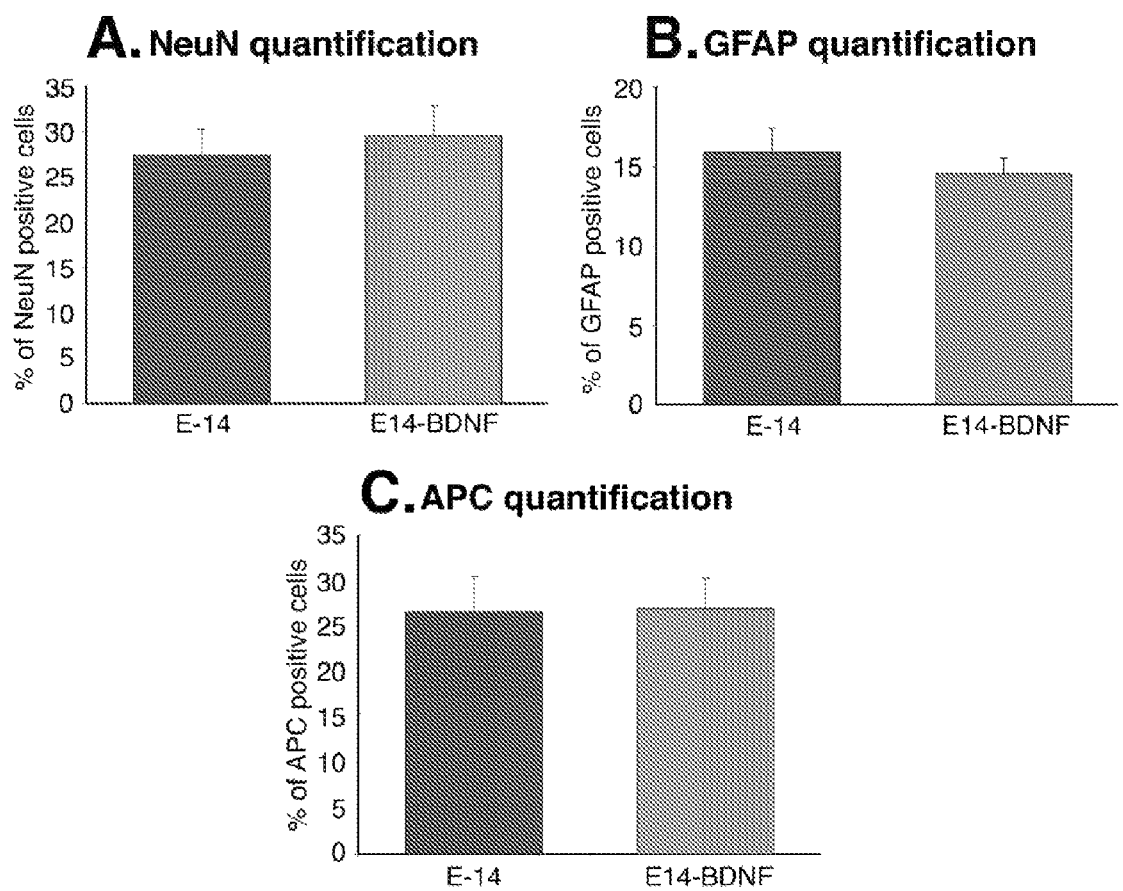
FIG. 11 shows (A) 25-30% of grafted E14-GFP-expressing cells express the neuron-specific marker NeuN when assessed 3 months post-grafting. Approximately 15% of grafted cells express the astrocyte marker GFAP (B) and 25% of grafted cells express the mature oligodendroglial marker APC. Co-injection of AAV2 vectors expressing BDNF into host spinal cord does not significantly alter these neuronal and glial proportions (Student's t-test: a, p=0.65; b, p=0.5 and c, p=0.91).
Figure 12:
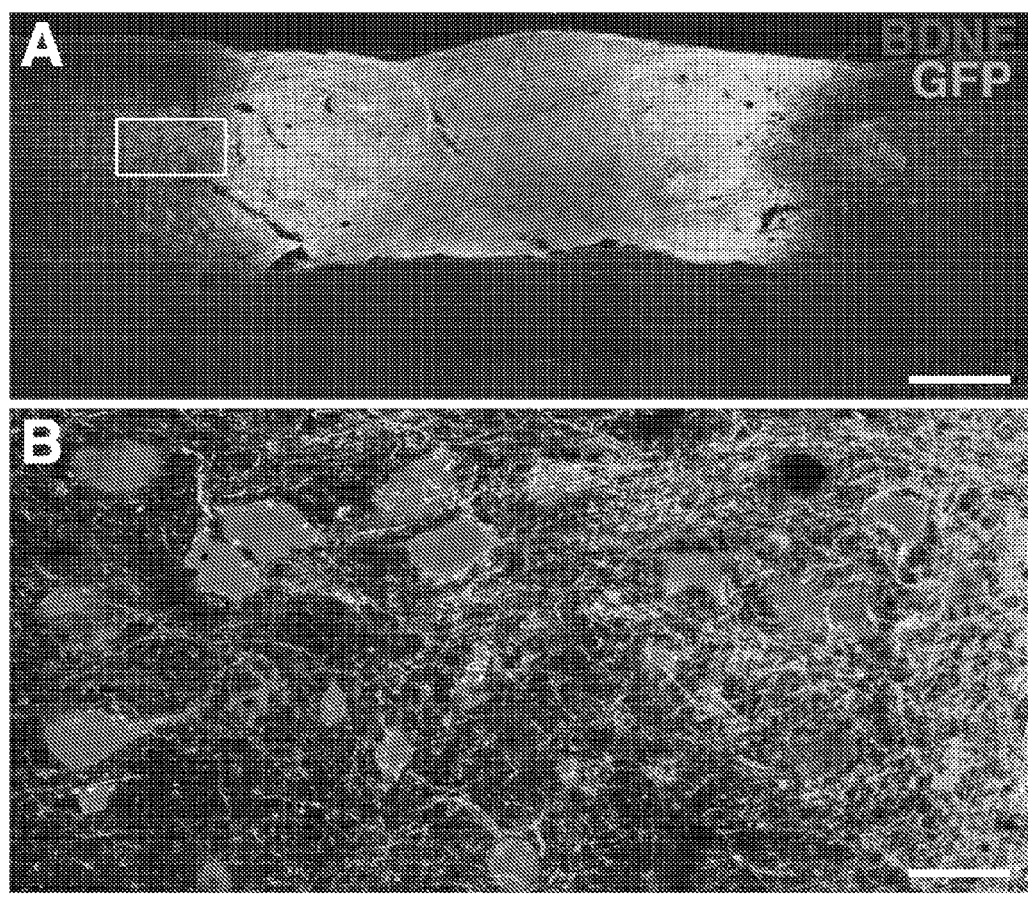
FIG. 12 shows (A, B) AAV2 vectors expressing BDNF were injected into host spinal cord parenchyma 1 mm rostral and 1 mm caudal to the lesion site in 10 animals. BDNF labeling is present in cells surrounding the lesion site; cells bear morphological characteristics of neurons. In (B), GFP neurite labeling, derived from E14 grafted tissue, is intercalated within regions of BDNF expression. Scale bar, A, 600 µm; B, 60 µm.

Cell Survival and Differentiation After Grafting to Adult Spinal Cord Lesion Sites Grafted cell suspensions survived and completely filled C5 hemisection and T3 complete transection lesion cavities, clearly revealed by GFP immunolabeling (FIG. 1). Grafted cells primarily differentiated into neurons (~25%) and oligodendroglia (~25%), together with astrocytes (~15%) (FIG. 1 and FIGS. 9-11). AAV2-BDNF injections into the host spinal cord 1 mm rostral and caudal to the lesion (FIG. 12) did not influence graft differentiation (FIG. 11). Numerous large GFP-labeled cells co-localized with the neuronal markers NeuN (FIG. 1), βIII tubulin (Tuj1) and MAP2 (FIG. 9). In addition to expressing mature neuronal markers, numerous grafted cells also expressed choline acetyltransferase (ChAT), characteristic of spinal motor neurons, and the inhibitory neuronal marker glutamic acid decarboxylase 67 (GAD67) (FIG. 9). The proportion of ChAT and GAD67-expressing neurons did not change in grafted subjects that received AAV2-BDNF injections (FIG. 9).

EXAMPLE VI

Figure 2:
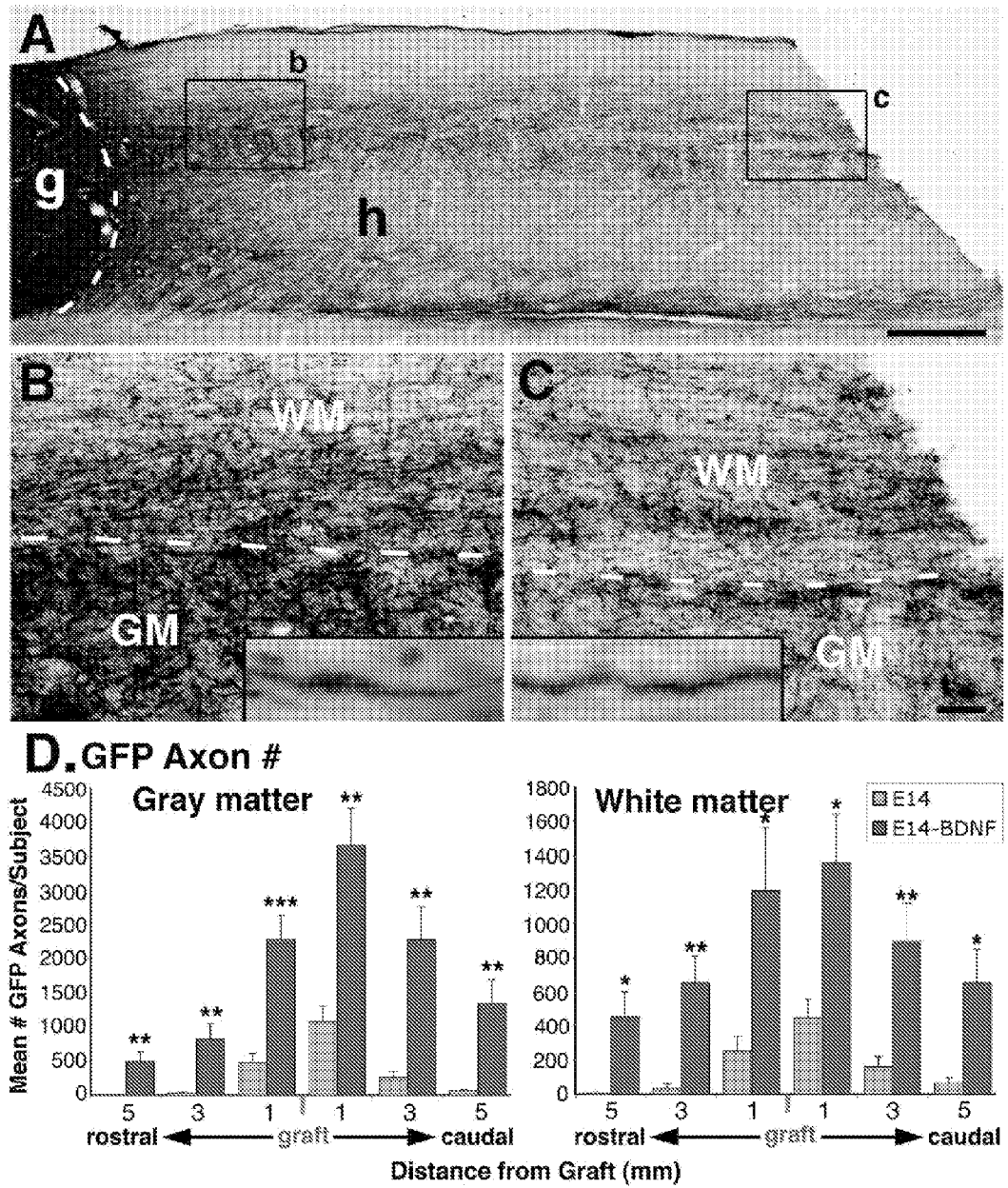
FIG. 2 relates to GFP-expressing embryonic neurons implanted into C5 hemisection lesion site robustly extend axons into host spinal cord. (A-C) shows GFP immunolabeling (dark cells) is specific for the cell bodies and processes of grafted E14 cells from GFP rats. An overview of the spinal cord at low magnification shows the remarkable extent to which neurons in the graft (g), left side of panel within dashed lines) extend processes in the adjoining host spinal cord (h). Indeed, extensive regions of the host spinal cord contain graft-derived projections in white matter (WM) and gray matter (GM), as show at higher magnification in panels B, C and insets from boxed regions of A. These GFP-labeled processes are axons, demonstrated by co-localization of GFP with the axonal marker neurofilament in FIG. 5. (D) Quantification of GFP-labeled axons in gray matter (left) and white matter (right) both rostral and caudal to lesion site (1, 3, and 5 mm from center of the graft). Subjects that received AAV2 BDNF gene delivery (n=10) into the host spinal cord adjoining the lesion site exhibit significantly greater numbers of GFP-labeled axons at all distances compared to the E14 group (n=6) (ANOVA $p<0.001$, then pooled t-test at each distance, *$p<0.05$; $p<0.01$; *$p<0.001$). Scale bar: a, 700 µm; b-c, 60 µm.
Figure 3:
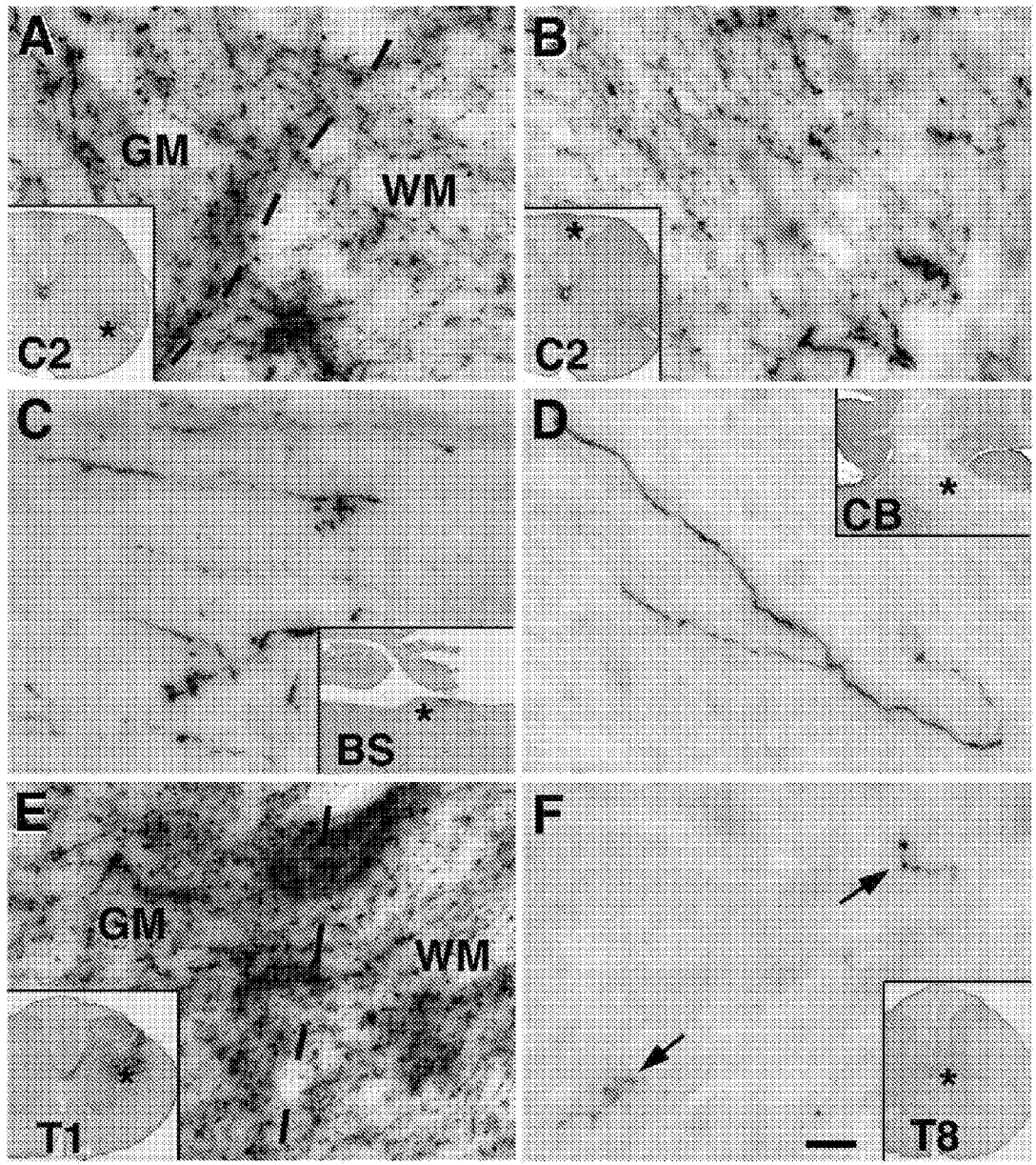
FIG. 3 relates to GFP-labeled axons extend into host spinal cord over remarkably long distances. (A) shows that a high density of (dark) GFP-labeled axons is present in ventrolateral portion of the C2 spinal segment after grafting to C5 hemisection lesion site. GM, gray matter; WM, white matter; dashed lines indicate gray/white interface. Star shows location of higher magnification view. (B) Numerous axons are also present in dorsal columns at C2 level. (C) GFP-labeled axons extend into brainstem (BS; overview show in inset), with labeling present in gracile and cunate nuclei. (D) Axons are present in cerebellar (CB) white matter (location indicated in lower magnification inset). (E) GFP-labeled axons also robustly extend caudally to T1 level in gray and white matter, and (F) as far caudally as T8. Overall, axons extend at least 35 mm total. Scale bar: 20 µm.
Figure 4:
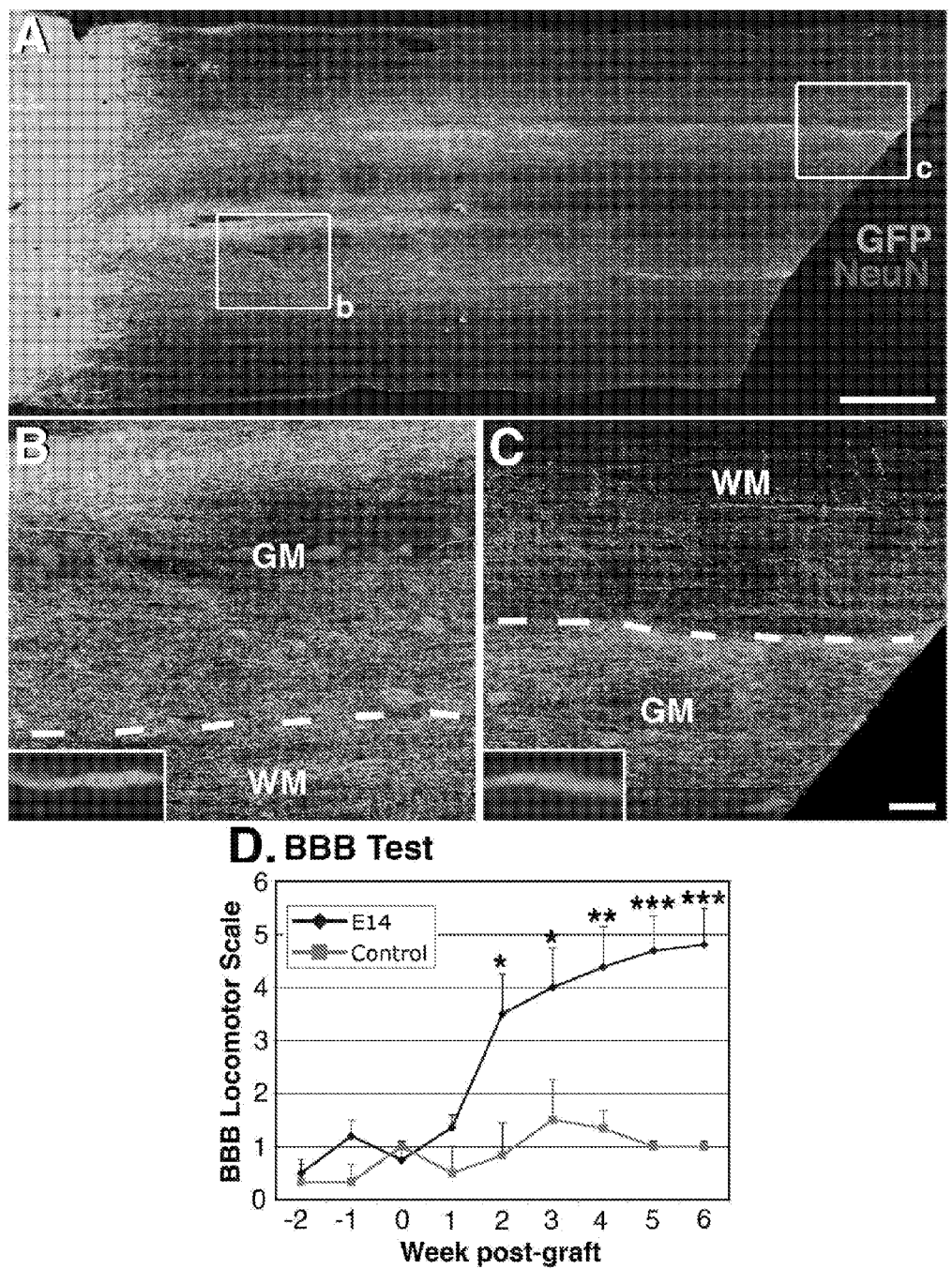
FIG. 4 shows that (A) GFP and NeuN double fluorescent labeling reveals that GFP-expressing grafts robustly extend axons into host spinal cord caudal and rostral to lesion after T3 complete transection (caudal shown). (B-C) Higher magnifications from boxed area of panel A show axons from graft extending into both gray matter (GM) and white matter (WM) through the entire 12 mm long horizontal section (see insets for individual axons). Dashed lines indicate gray/white matter interface. Scale bar: a-b, 310 µm; c, 550 µm; d-e, 64 µm. (D) BBB scores in subjects that underwent T3 complete transection (without BDNF delivery) show significant recovery in subjects that received embryonic grafts (n=8) compared to lesioned controls (n=3). Values are mean±SEM (Repeated measures Manova, $p<0.001$; Student's t-test for individual time points: *$p<0.05$, $p<0.01$, *$p<0.001$).
Figure 5:
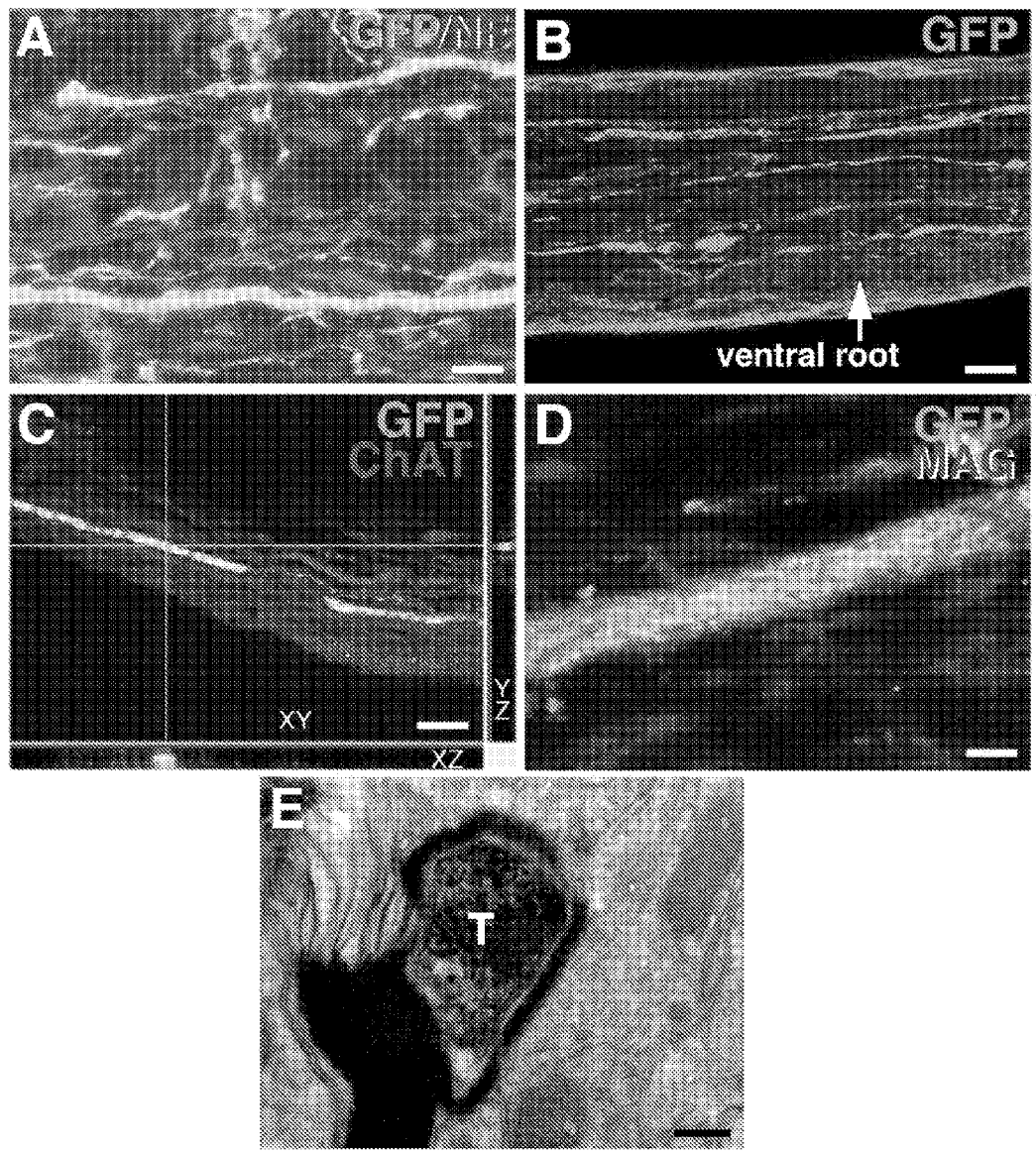
FIG. 5 shows that (A) GFP-labeled projections from grafted neurons express neurofilament (NF), confirming their identity as axons in the host spinal cord (region shown is host gray matter 1 mm caudal to lesion). (B) Projection of GFP-labeled axons into adjacent ventral roots 1 mm distal to root emergence from spinal cord. (C) GFP-labeled axons within ventral roots co-localize with the mature motor axonal marker ChAT (confocal z-stack with XY, XZ, and YZ views). (D) GFP-labeled axons are myelinated in many cases, (darker, myelin-associated glycoprotein, MAG); region shown is white matter 2 mm caudal to lesion site. (E) Electron micrograph showing myelination of a transplant derived axon (T). Dark reaction product within transplanted axon is GFP-immunoreactive material (region shown is white matter 2 mm caudal to lesion/graft site). Scale bar: A, 8 µm; B, 50 µm; C, 16 µm; D, 3 µm; E, 200 nm.
Figure 13:
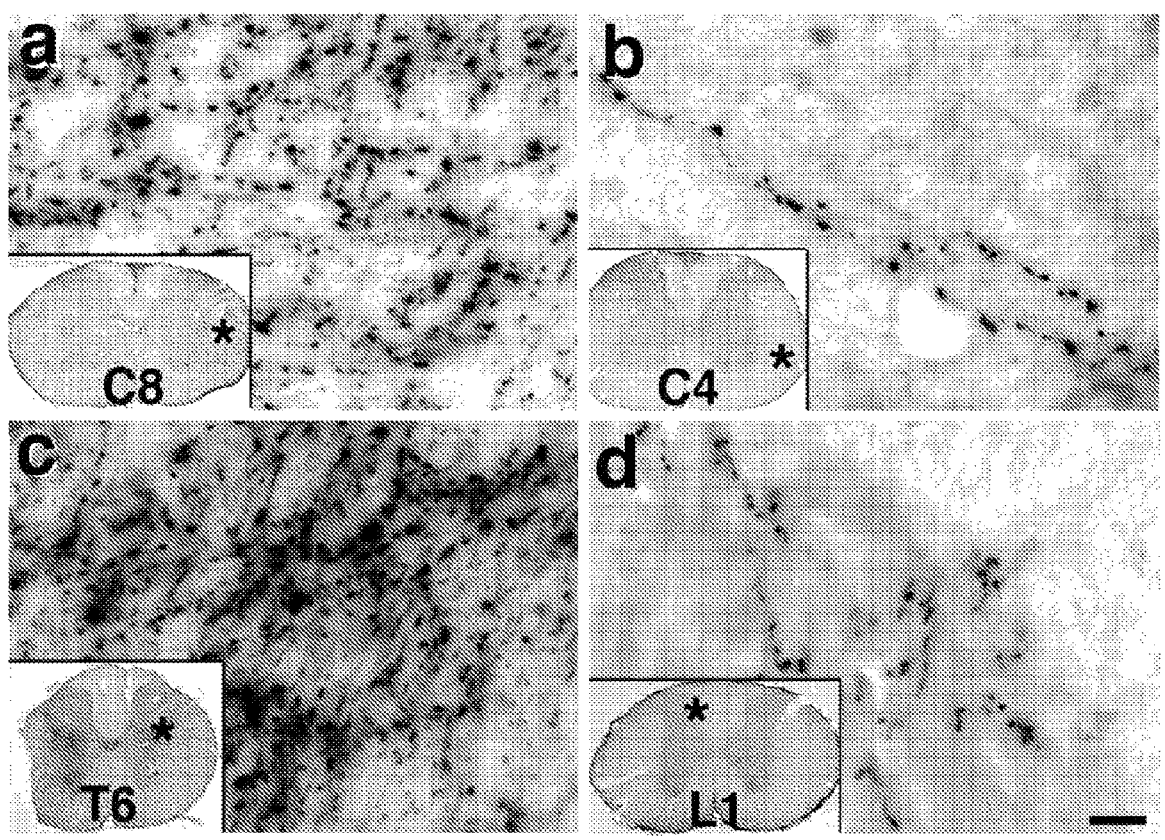
FIG. 13 shows (A) A high density of GFP-labeled axons is present in the lateral portion of the C8 spinal segment after grafting to a T3 complete lesion site. Star shows location of higher magnification view. (B) Several axons are also present in ventrolateral region of spinal cord at the C4 level. (C) GFP-labeled axons also robustly extend caudally to the T6 level in gray matter (shown) and white matter (not shown), and (D) as far caudally as the L1 level. Overall, axons extend at least 30 mm total. Scale bar: 10 µm.

Grafted Neurons Extend Large Numbers of Axons Over Long Distances in the Lesioned Adult Spinal Cord Grafted embryonic spinal cord neurons extended large numbers of axons into the host spinal cord in both rostral and caudal directions over remarkably long distances (FIGS. 2-4). Emerging GFP-labeled processes from grafts were axons, as demonstrated by co-labeling for the axonal marker neurofilament (FIG. 5). In the cephalad (rostral) direction, graft-derived axons extended as far as 15 mm from the C5 lesion cavity and into the brainstem (FIG. 3). Graft-derived axons also extended caudally as far as 30 mm to lower thoracic levels, a distance of more than 10 spinal segments (FIG. 3). Similarly, after T3 complete transection, GFP-labeled graft-derived axons grew extensively into the host spinal cord, extending rostrally into the upper cervical spinal cord and caudally into the lumbar spinal cord (FIG. 4 and FIG. 13).

Notably, axons extended in large numbers and over long distances in adult white matter, despite the presence of several known myelin-associated inhibitors. Similarly, axonal outgrowth from the graft/host interface was robust despite the deposition of the inhibitory extracellular matrix molecule chondroitin sulfate proteoglycan. In addition, grafted cells differentiating into neurons extended axons from the spinal cord lesion site into host ventral roots (FIG. 5). Most axons extending into ventral roots expressed the motor neuronal marker ChAT (FIG. 5). GFP-labeled axons were not detected in dorsal roots. Graft-derived axons in host white matter were frequently myelinated (FIG. 5). Recipients of BDNF-secreting vector injections exhibited a significant, 5-fold increase in the number of axons growing in both rostral and caudal directions ($p<0.05$; FIG. 2), but no change in the rostral-to-caudal distance over which axons extended into the host spinal cord.

These data demonstrate that grafted embryonic neurons extended large numbers of axons into the adult spinal cord over remarkably long distances. Axons extended rostrally from a mid-cervical lesion site into the brainstem, and caudally over more than half the distance of the remaining spinal cord; axons of grafted neurons also exited the spinal cord and regenerated into ventral motor roots. Grafted neurons differentiated into multiple neuronal phenotypes, including motor neurons. Axons emerging from grafts formed abundant synapses of both excitatory and inhibitory phenotypes with host neurons.

The density but not distance of axon outgrowth was enhanced by viral delivery of brain-derived neurotrophic factor (BDNF). These findings indicate that intrinsic neuronal properties can overcome the inhibitory milieu of the adult CNS to mount remarkably extensive axonal growth.

EXAMPLE VII

Integration and Synapse Formation with Host Spinal Cord Circuitry

Figure 6:
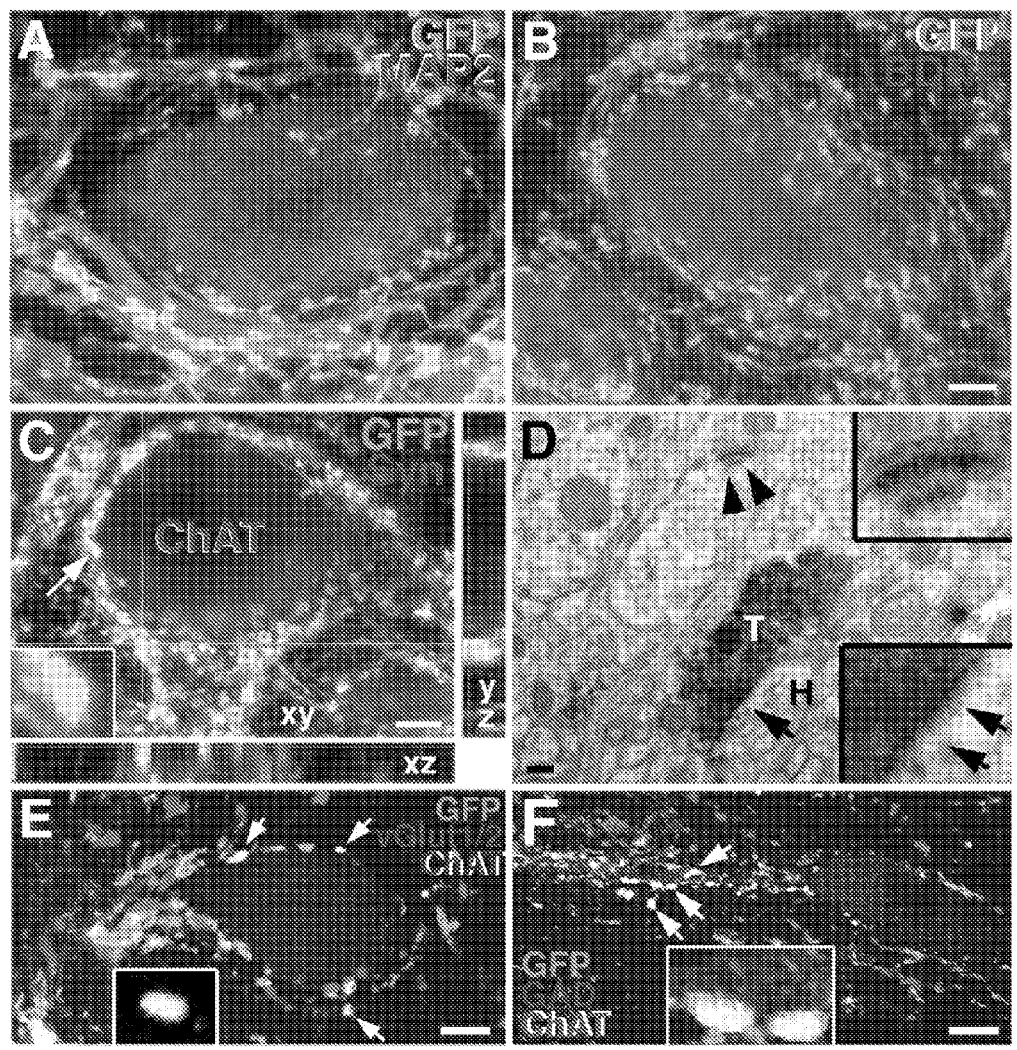
FIG. 6 shows that (A) In an embryonic GFP-grafted subject, graft-derived GFP-expressing axons are closely associated with host MAP-2-expressing neurons and dendrites 2 mm caudal from lesion site. (B) The number of graft-derived GFP-expressing axons is greater when the host spinal cord is injected with AAV2-BDNF expressing vectors; shown is a host neuron expressing BDNF densely surrounded by GFP-expressing, graft-derived axons with bouton-like terminals. (C) A z-stack image triple labeled for GFP, synaptophysin (Syn), and ChAT, indicating co-association of graft-derived axons with a synaptic marker in direct association with host motor neurons. Inset shows double labeling of GFP and synaptophysin. (D) Electron microscopy confirms that graft-derived axons make synaptic contact with host: DAB-labeled GFP-expressing axon terminal forms a synapse (arrow) with host dendrite, shown at higher magnification in inset. For comparison, arrowheads indicate a synapse from a host axon with the same host dendrite (inset in upper right corner). (E-F) Triple fluorescent labeling for GFP; vesicular glutamate transporters 1/2 (vGlut1/2) or glutamic acid decarboxylase 65 (GAD), and choline acetyltransferase (ChAT) shows (E) expression of vGlut1/2 by axons of some grafted neurons (arrows), with one double-labeled terminal shown in inset, and (F) expression of the inhibitory transmitter GAD65 by other grafted axon terminals in close association with host motor (ChAT-labeled) neurons. Scale bar: a, b, c, 8 µm; d, 200 nm; e, 7 µm; f, 6 µm.
Figure 7:
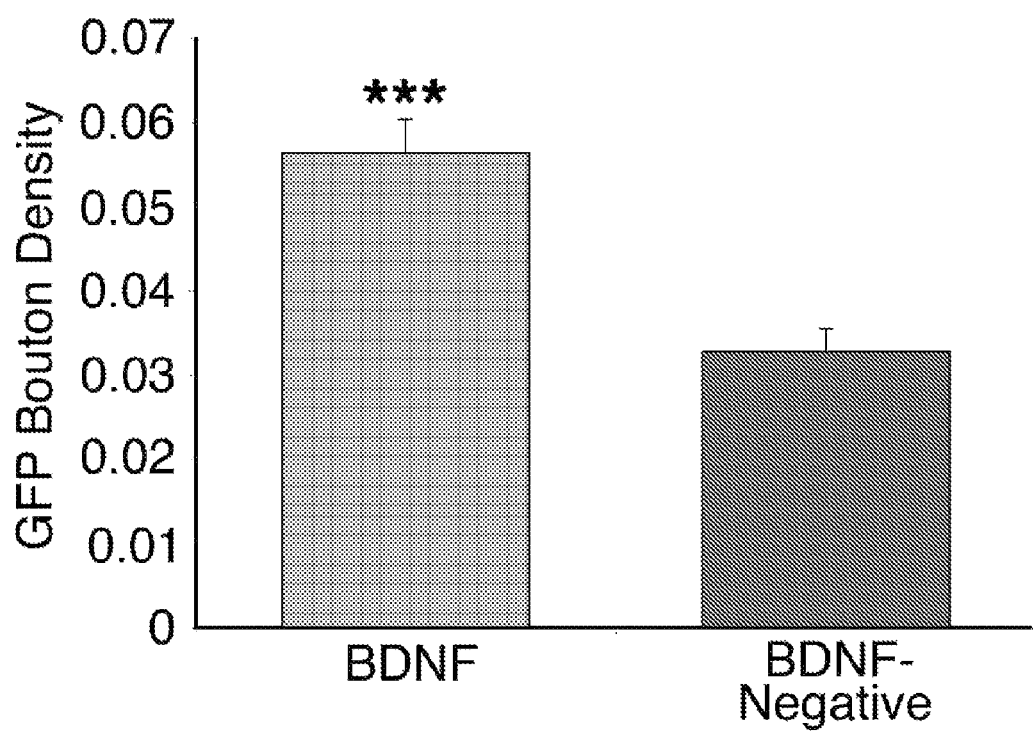
FIG. 7 shows quantification of GFP-labled axonal terminal boutons surrounding neuronal somata 1 mm caudal to the lesion/graft site. A significant increase in the density of terminal boutons around BDNF-expressing neuronal somata compared to host neurons not expressing BDNF is shown (two-tailed Student's t-test, p>0.0001).

GFP-labeled, graft-derived axons in the host spinal cord formed dense bouton-like terminals around host dendrites and cell bodies, identified by labeling for the neuronal markers MAP-2 and ChAT (FIG. 6). Clusters of GFP-labeled terminals were significantly denser around host neurons infected with the AAV2-BDNF gene ($p<0.0001$; FIG. 6 and FIG. 7), suggesting a chemotactic attraction of graft-derived axons to the growth factor. Double immunofluorescent labeling for GFP and synaptophysin suggested synapse formation between grafted and host neurons (FIG. 6). Immunoelectron microscopy confirmed synapse formation between GFP-labeled graft-derived axons and host neurons and dendrites (FIG. 6). Further, GFP-labeled terminal boutons expressed either the excitatory transmitter marker vesicular glutamate transporter 1/2 (vGlut1/2) or the inhibitory marker glutamic acid decarboxylase 65 (GAD65) (FIG. 6). Many instances of co-localization of these terminal region markers with ChAT were also found (FIG. 6).

Collectively, these findings demonstrate exuberant projections of embryonic graft-derived axons from sites of spinal cord injury into the adult spinal cord together with synapse formation, despite the presence of an intrinsically inhibitory environment in the adult spinal cord.

EXAMPLE VIII

Host Axons Penetrate Grafts and Express Synaptic Markers

Figure 8:
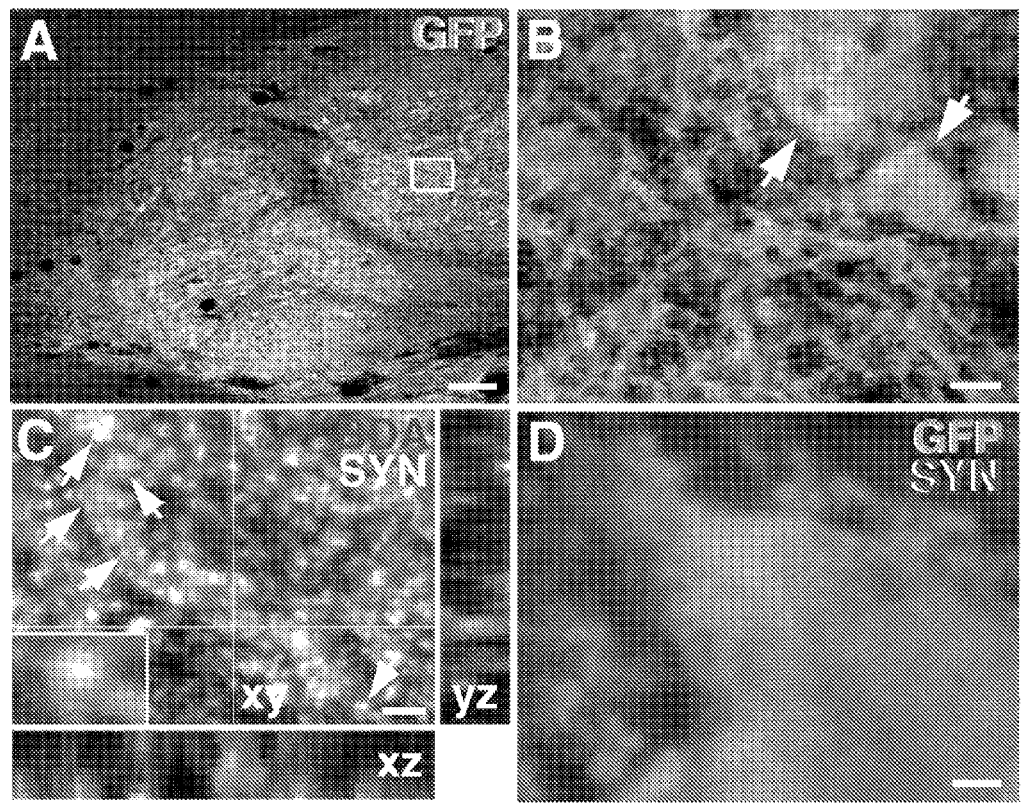
FIG. 8 shows that (A-B) Host reticulospinal axons labeled with BDA regenerate into GFP-expressing embryonic grafts in site of T3 complete transection (B, from boxed area of panel A; arrows indicate GFP-labeled grafted cells with neurology morphology). (C) Bouton-like structures on host reticulospinal axons (BDA) regenerating into graft co-localize with synaptophysin in a Z-stack image (arrows). (D) Host synaptophysin terminals are closely apposed to GFP-labeled grafted cells exhibiting neuronal morphology. (E) Overexpression of BDNF by grafted cells in the lesion site significantly enhances penetration of host BDA-labeled reticulospinal axons into C5 hemisection graft/lesion site. E14-BDNF group, n=10; E14 group, n=6 (Two-tailed Student's t-test ***p<0.001).
Figure 8:
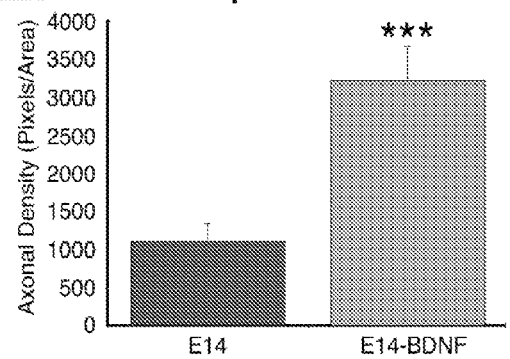

Host axons also penetrated embryonic grafts in spinal cord lesion sites (FIG. 8 and FIG. 14). Host inputs into grafts were both locally and supraspinally derived, and were greater in number when AAV2-BDNF was injected 1 mm from the host/graft interface ($p<0.001$; FIG. 8). Like graft-derived axons emerging from lesion sites, host axons penetrating grafts co-localized with the synaptic marker synaptophysin (FIG. 8), likely representing host-to-graft connectivity. These findings demonstrate that treatment of lesions according to the invention not only provides regeneration and recovery within the lesion site, but also aids in forming corticospinal axonal regeneration into the lesion site.

EXAMPLE IX

Functional Outcomes of Spinal Cord Injury Treatment

As discussed above, functional outcomes were measured in subjects that underwent T3 complete spinal cord transections and grafts two weeks later of embryonic GFP-expressing grafts to the lesion site (FIG. 4) (AAV2-BDNF was not administered).

Hindlimb locomotion was severely impaired in both lesion control and grafted subjects for three weeks post-injury; in the 4$^{th}$ week (two weeks post-grafting), recipients of embryonic GFP-expressing grafts exhibited significant improvement on the BBB scale (Basso et al., *Exp. Neurol.*, 139, 244-256 (1996)) that reached a plateau by 8 weeks post-lesion ($p<0.001$).

EXAMPLE X

Failure of Neuronal Differentiation and Support from Post-Natal and Adult Cell Grafts Lesions in animals prepared as described hereinabove were treated with either day 1 post-natal neural tissue cells or adult neural tissue cells. GFP, GFAP and NeuN triple labeling of histological samples was performed.

The day 1 post-natal cells had survived two months post-treatment. However, the grafted cells only extended processes for short distances into host tissue. Further, no cells showed NeuN expression, indicating lack of neuronal differentiation (FIG. 15).

Figure 16:
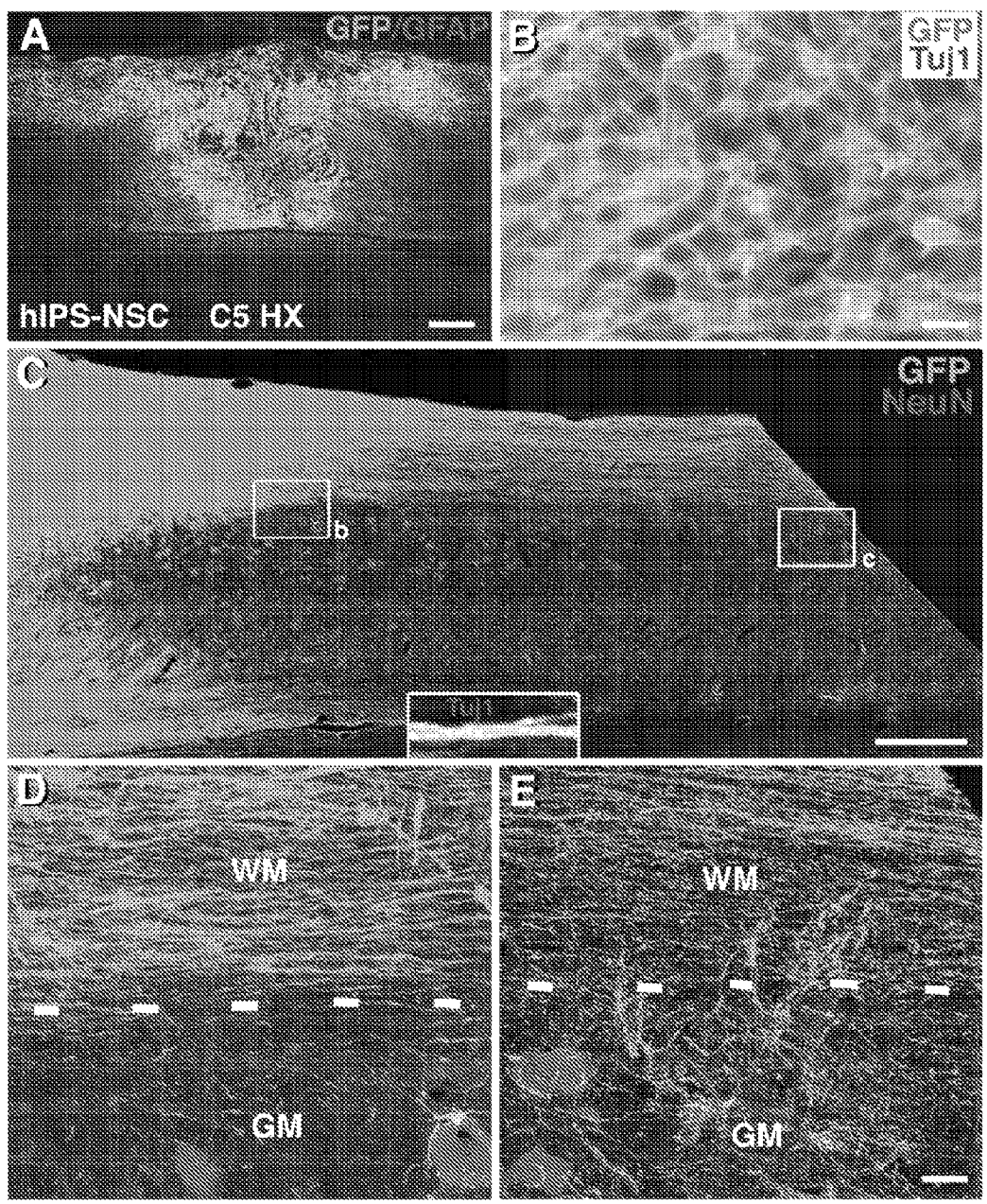
FIG. 16 shows (A) GFP-labeled human IPS cells (NDC1) derived neural stem cells grafted into sites of C5 hemisected spinal cord outlined by GFAP labeling survived well and filled up lesion cavity two months post-grafting. (B) Most grafted cells were TUJ1 positive, indicating neuronal differentiation. (C-E) Large numbers of GFP-labeled axons (co-localized with TUJ1, see inset) extended rostrally (not shown) and caudally (showed) into host spinal cord labeled with a neuronal marker, NeuN. (D-E) Higher magnification view from boxed area of panel C, dashed line indicate white matter (WM) and gray matter (GM) interface. Scale bar: A, 350 µm; B, 10 µm; C, 600 µm; D-E, 32 µm.

In animals treated with the adult cells, survival at the two month post-treatment point was poor and processes were also short. No cells showed NeuN expression, indicating lack of neuronal differentiation (FIG. 16).

EXAMPLE XI

Practice of the Invention with Human Induced Pluripotent Stem Cells

Human neural stem cells derived from induced pluripotent stem cells (IPSCs) also exhibit extensive growth and connectivity when grafted into rodent models of spinal cord injury. A human IPS derived neural stem cell line expressing GFP was transplanted into C5 lateral hemisection spinal cord injury sites in immune-deficient rats. Treatment included a fibrin matrix and growth factor cocktail as described in previous examples.

Figure 17:
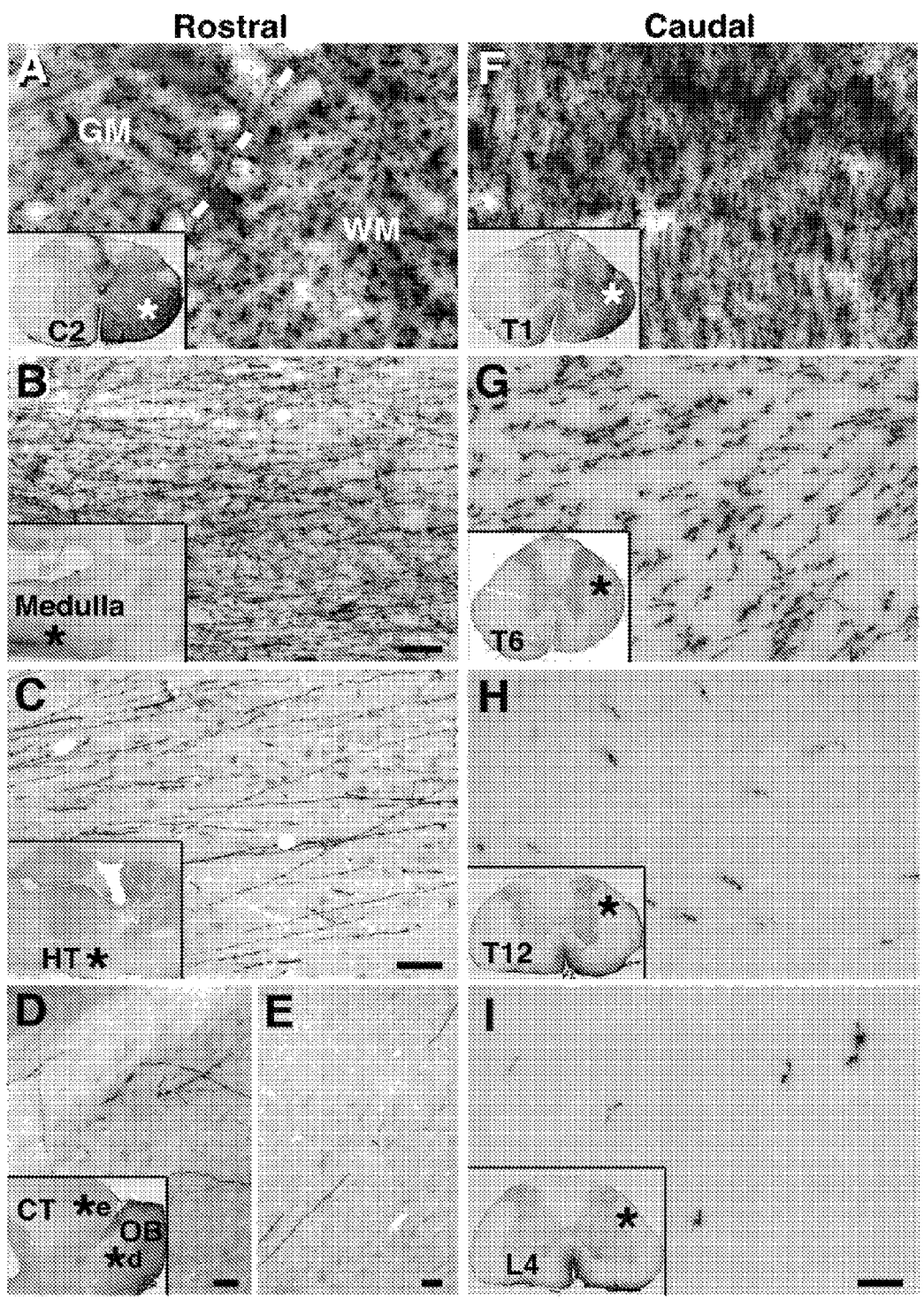
FIG. 17 shows (A-E) Large numbers of GFP-labeled axons from C5 hemisection site extend rostrally into (A) host spinal cord (C2 shown) and many regions of brain, including (B) medulla, (C) hypothalamus (HT), (D) cortex (CT) and (E) olfactory bulb (OB). Asterisks indicate location of higher magnification views. (F-I) GFP-labeled axons also extend in high density caudal to T1, T6, T12 and L4, Overall, axons extend almost into entire rat CNS, at least 40 mm in each direction. Scale bar: A, F-I, 20 µm; B-C, 80 µm; D, 30 µm E, 50 µm.
Figure 18:
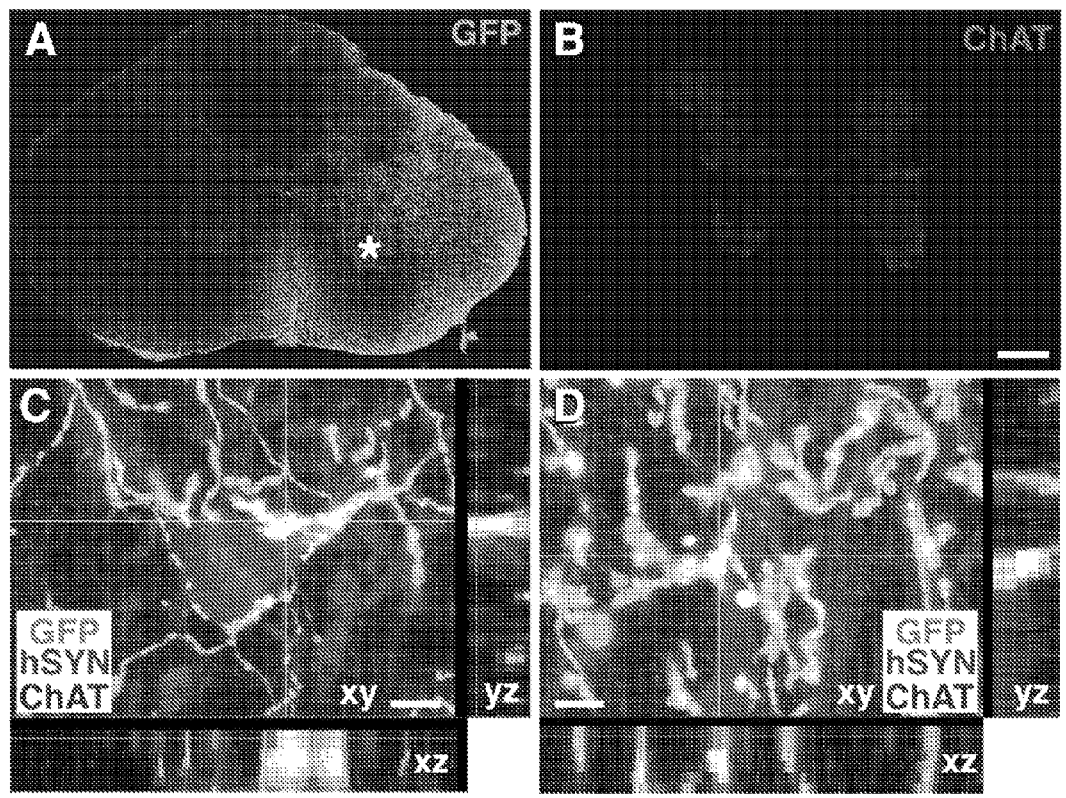
FIG. 18 shows (A-B) GFP and ChAT labeling demonstrate distribution of GFP labeled axons derived from human IPS cells at T1 level, 3 segments below graft. (C-D) GFP, human-specific synaptophysin (hSYN), and ChAT triple labeling in z-stacks reveals expression of hSYN in GFP-labeled axons that were surrounding host ChAT labeled motor neuron (C) soma and (D) neurites. Scale bar: A-B, 250 µm; C, 6 µm; D, 4 µm.
Figure 19:
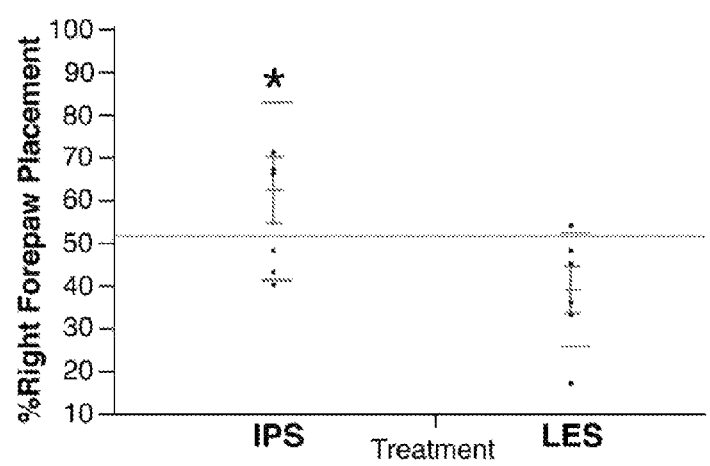
FIG. 19 shows significant functional outcome improvement on the grid-walking task in week 9 post-grafting in IPS cells grafted rats (n=7) than lesioned controls (LES, n=6) (*p<0.05).

On post-mortem examination two months later, grafted IPSC-derived neural stem cells survived and differentiated into numerous neurons that extended large numbers of axons that reached almost the entire length of the rat central nervous system Axons extended rostrally to the olfactory bulb and caudally to the lumbar cord. Axons emerging from grafts expressed synaptophysin, suggesting synaptic connections with the host (FIGS. 17-19). Rats receiving neural stem cell grafts performed significantly better in grid-walking test than non-grafted lesioned rats (FIG. 20).

These findings indicate that human IPSC-derived neural stem cells have intrinsic growth and connectivity capacity after spinal cord injury similar to pluripotent embryonic stem cells as described herein, offering significant potential to repair the nervous system after injury.

claim 1. A method for treating a lesion in the post-embryonic spinal nerves of a subject, the method consisting essentially of;
(a) administering treatment to the spinal nerves by grafting human pluripotent neural stem cells evenly distributed throughout a transplantation matrix comprising fibrin together with brain-derived neurotrophic factor (BDNF) into the lesion or no more than up to 1 mm away therefrom by injection or infusion;
(b) determining pre- and post-treatment locomotor function in the subject, wherein, notwithstanding the inhibitory mileau of chondroitin sulfate proteoglycan in the spinal cord, stimulated axonal growth in response to the administering step provides clinically significant restoration in locomotor function of spinal nerves from the lesioned site in the subject comparable to significant improvement on the Basso, Beattie, and Bresnahan (BBB) scale.

What is claimed is:

1. A method for treating a lesion in the post-embryonic spinal nerves of a subject, the method consisting essentially of;
(a) administering treatment to the spinal nerves by grafting human pluripotent neural stem cells evenly distributed throughout a transplantation matrix comprising fibrin together with brain-derived neurotropic factor (BDNF) into the lesion or no more than up to 1 mm away therefrom by injection or infusion;
(b) determining pre- and post-treatment locomotor function in the subject, wherein, notwithstanding the inhibitory mileau of chondroitin sulfate proteoglycan in the spinal cord, stimulated axonal growth in response in the locomotor function of spinal nerves from the lesioned site in the subject comparable to significant improvement on the Basso, Beattie, and Bresnahan (BBB) scale.

2. The method according to claim 1, wherein the pluripotent neural stem cells are N1 stage or earlier cells.

3. The method according to claim 1, wherein the pluripotent neural stem cells are of embryonic mammalian origin.

4. The method according to claim 1, wherein the pluripotent neural stem cells are induced pluripotent cells of post-natal mammalian origin.

5. The method according to claim 1, wherein the total concentration of BDNF administered is from 1 fg protein/ml of pharmaceutically acceptable composition to 1 mg of protein/ml of pharmaceutically acceptable composition.

6. The method according to claim 1, wherein the BDNF is expressed in situ from a recombinant expression vector, wherein said expression provides an equivalent of 1 fg protein/ml of pharmaceutically acceptable composition to 1 mg of protein/ml of pharmaceutically acceptable composition.

7. The method according to claim 1, wherein the lesion is fully filled by the neural stem cells and transplantation matrix.

8. The method according to claim 1, wherein the concentration, of neural stem cells grafted is from 10,000 to 500,000 cells/ml of transplantation matrix.

9. The method according to claim 1, wherein new synaptic junctions with neurons are formed at the termini of the growing axons.

10. The method according to claim 1, wherein the subject is human.

11. A method for treating a lesion in the post-embryonic spinal nerves of a subject, the method consisting essentially of administering treatment to the spinal nerves by grafting human pluripotent neural stem cells evenly distributed throughout a transplantation matrix comprising fibrin as well as brain-derived neurotrophic factor (BDNF) into the lesion or no more than 1 mm away therefrom by injection or infusion;
wherein, notwithstanding the inhibitory mileau of chondroitin sulfate proteoglycan present in the spinal cord, nerve cell differentiated grafted neural stem cells are clinically confirmed to respond to the treatment by increasing in outgrowth from the lesion by up to 5 fold in density, graft-derived axons extend up to 30 mm rostrally and caudally from the administration site and new synaptic junctions with neurons are formed at the termini of the growing axons;
wherein further the stimulated axonal growth provides clinically significant restoration in locomotor function of spinal nerves in the lesioned site.

12. The method according to claim 11, wherein the transplantation matrix further comprises thrombin.

13. The method according to claim 11, further comprising the step of determining the pre- and post-treatment locomotor function in the subject, wherein the stimulated axonal growth in response to the administering step provides clinically significant restoration in locomotor function of spinal nerves from the lesioned site in the subject comparable to significant improvement on the BBB scale.

* * * * *